United States Patent
Milbocker et al.

(10) Patent No.: US 10,507,015 B2
(45) Date of Patent: Dec. 17, 2019

(54) LOW NORMAL FORCE RETRACTING DEVICE COMPRISING A MICROTEXTURED SURFACE

(71) Applicant: BVW Holding AG, Cham (CH)

(72) Inventors: Michael Milbocker, Holliston, MA (US); Lukas Bluecher, Eurasburg (DE)

(73) Assignee: BVW Holding AG, Cham (CH)

( * ) Notice: Subject to any disclaimer, the term of this patent is extended or adjusted under 35 U.S.C. 154(b) by 158 days.

(21) Appl. No.: 15/285,516

(22) Filed: Oct. 5, 2016

(65) Prior Publication Data
US 2017/0095242 A1 Apr. 6, 2017

Related U.S. Application Data

(60) Provisional application No. 62/237,448, filed on Oct. 5, 2015.

(51) Int. Cl.
| | |
|---|---|
| *A61B 1/32* | (2006.01) |
| *A61B 17/02* | (2006.01) |
| *A61B 17/00* | (2006.01) |

(52) U.S. Cl.
CPC .......... *A61B 17/0218* (2013.01); *A61B 17/02* (2013.01); *A61B 2017/0096* (2013.01);
(Continued)

(58) Field of Classification Search
CPC ............... A61B 17/0218; A61B 17/02; A61B 2017/00557; A61B 2017/00858;
(Continued)

(56) References Cited

U.S. PATENT DOCUMENTS 5,545,122 A * 8/1996 Spruill .................. A61B 1/015
600/186
6,994,045 B2 2/2006 Paszkowski
(Continued)

FOREIGN PATENT DOCUMENTS

| WO | 199221295 | 12/1992 |
|---|---|---|
| WO | 199815229 | 4/1998 |

(Continued)

*Primary Examiner* — Jessica Weiss
(74) *Attorney, Agent, or Firm* — Patterson Intellectual Property Law, P.C.; Ryan D. Levy; Mark A. Kilgore

(57) ABSTRACT

Retraction of one or more three-dimensional or planar amorphous objects is provided to gain access for a procedure where the retracted elements are easily damaged by application of normal forces. For example, a surgical instrument to provide access to an organ or tissue plane. Microtextured surfaces are provided that provide immobilization of amorphous objects, the immobilization of which is characterized by low normal forces and high shear or in plane forces. The retraction device is comprised of microstructured surfaces on one or more arms. Preferably these arms are soft and flexible to minimize damage to retracted objects. In some instances, these arms resemble and are used as a nonslip tape. Alternatively, parts or whole arms of the retraction device are rigid to provide a supportive aspect. These arms may be configured around a handle. Furthermore, the microtextured aspect may be further augmented with conventional gripping surfaces, such as a sticky surface, or a surface comprised of one or more hooks or barbs. The handle means may be distributed over the retraction device, for example, holes distributed along the arms through which anchoring means are tied. The retraction device is particularly well suited for grasping wet, oily, slimy or living surfaces by applying a small nondestructive normal force.

12 Claims, 17 Drawing Sheets

(52) U.S. Cl.
CPC ............... *A61B 2017/00557* (2013.01); *A61B 2017/00858* (2013.01); *A61B 2017/00938* (2013.01); *A61B 2017/0225* (2013.01); *A61B 2017/0237* (2013.01); *A61B 2017/0243* (2013.01); *A61B 2217/005* (2013.01)

(58) Field of Classification Search
CPC .. A61B 2017/00938; A61B 2017/0096; A61B 2017/0225; A61B 2017/0237; A61B 2017/0243; A61B 2217/005
USPC .................................................. 600/200–249
See application file for complete search history.

(56) References Cited

U.S. PATENT DOCUMENTS

| | | | |
|---|---|---|---|
| 7,419,615 B2 | 9/2008 | Strauss | |
| 7,887,736 B2 | 2/2011 | Lee et al. | |
| 2003/0147932 A1 | 8/2003 | Nun et al. | |
| 2005/0137460 A1* | 6/2005 | Bertolero | A61B 17/02 600/213 |
| 2006/0029808 A1 | 2/2006 | Zhai et al. | |
| 2006/0247500 A1* | 11/2006 | Voegele | A61B 1/32 600/208 |
| 2007/0156023 A1* | 7/2007 | Frasier | A61B 17/0293 600/206 |
| 2008/0015298 A1 | 1/2008 | Xiong et al. | |
| 2008/0241512 A1 | 10/2008 | Boris et al. | |
| 2009/0011222 A1* | 1/2009 | Xiu | C23C 18/00 428/323 |
| 2009/0076430 A1 | 3/2009 | Simpson et al. | |
| 2009/0227164 A1 | 9/2009 | Broch-Nielsen et al. | |
| 2009/0259089 A1* | 10/2009 | Gelbart | A61M 1/1037 600/16 |
| 2009/0294732 A1* | 12/2009 | Atanasoska | A61L 29/085 252/500 |
| 2010/0021692 A1 | 1/2010 | Bormashenko et al. | |
| 2010/0028604 A1 | 2/2010 | Bhushan et al. | |
| 2010/0112286 A1 | 5/2010 | Bahadur et al. | |
| 2011/0077172 A1 | 3/2011 | Aizenberg et al. | |
| 2011/0150765 A1* | 6/2011 | Boyden | A61K 9/0019 424/9.1 |
| 2012/0130182 A1* | 5/2012 | Rodrigues, Jr. | A61B 17/3423 600/206 |
| 2012/0143010 A1* | 6/2012 | Deasey | A61B 17/02 600/207 |
| 2012/0276334 A1* | 11/2012 | Fedynyshyn | B05D 5/04 428/141 |
| 2013/0011332 A1* | 1/2013 | Boyden | A61M 37/0015 424/1.11 |
| 2013/0178722 A1* | 7/2013 | Aria | A61K 9/0021 600/309 |
| 2014/0249448 A1* | 9/2014 | Furlong | A61B 10/04 600/563 |
| 2014/0276407 A1* | 9/2014 | Devries | A61B 17/22032 604/103.08 |
| 2014/0336444 A1* | 11/2014 | Bonde | A61M 1/1086 600/16 |
| 2015/0018710 A1* | 1/2015 | Furlong | A61B 1/00094 600/563 |
| 2015/0018711 A1* | 1/2015 | Furlong | A61B 1/012 600/565 |
| 2015/0031951 A1* | 1/2015 | Furlong | A61B 1/00094 600/106 |
| 2015/0032024 A1* | 1/2015 | Furlong | A61B 10/04 600/563 |
| 2015/0289751 A1* | 10/2015 | Frerck | A61B 1/00135 600/121 |
| 2015/0366462 A1* | 12/2015 | Ramos | A61B 5/01 600/549 |
| 2017/0014111 A1* | 1/2017 | Hulseman | A61B 17/00 |

FOREIGN PATENT DOCUMENTS

| | | | | |
|---|---|---|---|---|
| WO | 2005042646 | 5/2005 | | |
| WO | 2013044151 | 3/2013 | | |
| WO | WO 2013112378 A2 * | 8/2013 | ............. | A61L 27/34 |

\* cited by examiner

LOW NORMAL FORCE RETRACTING DEVICE COMPRISING A MICROTEXTURED SURFACE

RELATED APPLICATIONS

This application claims the benefit of U.S. provisional application No. 62/237,448 filed on Oct. 5, 2015, the contents of which are hereby incorporated by reference in their entirety.

TECHNICAL FIELD

The present disclosure relates to surgical retractors comprising microtextured surfaces. The surgical retractors comprise a microtextured surface on one or more portions of the retractor, thereby advantageously providing immobilizing or positioning forces to a wet tissue surface while preventing or minimizing damage or trauma to the tissue.

BACKGROUND

There are many objects, natural and manmade, that are characterized by possessing a relatively durable surface enclosing delicate structures that would be adversely altered by a force applied normal to the durable surface and unaltered by a force applied tangent or in plane to the durable surface. Therefore, there is a need in the art for a retracting device that allows these objects to be immobilized, relocated, or positioned without causing internal damage by the force applied by the retractor.

A non-limiting example is the traction of living tissue during a medical procedure such as a surgery. In these procedures it is frequently necessary to retract organs to gain access to a target organ or tissue to be treated or observed. In other procedures, to gain access to the organ or tissue to be treated or observed, it is necessary to separate the organ to be treated from tissue surrounding it. For example, to be able to observe the outer surface of the heart, it must be separated from the pericardium. To obtain the necessary retraction, current laparoscopic procedures use several small retractors inserted through a plurality of incisions. Because such retractors have a relatively small surface area, they tend to damage and/or cause trauma to the retracted organs or tissue by applying localized normal forces.

Wenzel, Cassie and Wenzel-Cassie states describes wetting phenomena between hydrophobic and hydrophilic components of a mixture at a surface interface. The interaction of a solid textured surface with water in a gaseous environment is described by the Cassie-Baxter model. In this model, air is trapped in the microgrooves of a textured surface and water droplets rest on a compound surface comprising air and the tops of microprotrusions. The importance of a fractal dimension between multiple scales of texture is well recognized and many approaches have been based on the fractal contribution, i.e., the dimensional relationship between different scales of texture.

However, regardless of the material (organic or inorganic) used and geometric structure of a surface texture (particles, rod arrays, or pores), multiple scales of texture in combination with low surface energy would be needed to obtain the so called superhydrophobic surfaces. Superhydrophobicity is variously reported as a material exhibiting a contact angle with water that is greater than contact angles achievable with smooth but strongly hydrophobic materials. The general consensus for the minimum contact angle for a superhydrophobic substance is 150 degrees.

A hydrophobic surface repels water. The hydrophobicity of a surface can be measured, for example, by determining the contact angle of a drop of water on a surface. The contact angle can be measured in a static state or in a dynamic state. A dynamic contact angle measurement can include determining an advancing contact angle or a receding contact angle with respect to an adherent species such as a water drop. A hydrophobic surface having a small difference between advancing and receding contact angles (i.e., low contact angle hysteresis) results in surfaces with low resistance to in plane translation (low adherence). Water can travel across a surface having low contact angle hysteresis more readily than across a surface having a high contact angle hysteresis, thus the magnitude of the contact angle hysteresis can be equated with the amount of energy needed to move a substance.

The classic motivation from nature for surface texture research is the lotus leaf, which is superhydrophobic due to a hierarchical structure of convex cell papillae and randomly oriented hydrophobic wax tubules, which have high contact angles and low contact angle hysteresis with water and show strong self-cleaning properties. A lesser known motivation from nature is the red rose petal, with a hierarchical structure of convex cell papillae ornamented with circumferentially arranged and axially directed ridges, which have a moderate contact angle and high angular contact difference.

The contact angle is a measure of the amount of water directly in contact with the textured surface, while the contact angle hysteresis is a measure of the degree to which water is mobile on a surface. The evolutionary motivation for each of these states is quite distinct. In the case of the lotus leaf, and botanical leaves generally, minimal contact with water and high water mobility results in preferential adherence of the water to particulate contaminants, which are cleared from the leave as the water runs off. This serves to reduce to the amount of light absorbance by surface contaminants, and increase photosynthetic efficiency. In the case of the rose petal, and botanical petals generally, most pollinators are attracted to high tension water sources which provide ready accessibility without drowning the insect. Thus, high contact angle paired with high contact angle hysteresis is preferred where the evolutionary stimulus is reproduction in botanicals, and high contact angle paired with low contact angle hysteresis is preferred where the evolutionary stimulus is metabolism and growth.

Considering for a moment a single texture scale, when water is placed on a textured surface it can either sit on the peaks of the texture or wick into the valleys. The former is called the Cassie state, and the later the Wenzel state. When the Wenzel state is dominant, both the contact angle and contact angle hysteresis increase as the surface roughness increases. When a roughness factor exceeds a critical level, however, the contact angle continues to increase while the hysteresis starts decreasing. At this point, the dominant wetting behavior changes, due to an increase in the amount of hydrophobic component (in this case, air) at the interface between the surface and water droplet. When multiple texture scales are employed, some can be Wenzel and others Cassie. Of the two states, the Wenzel state has the lower contact angle, higher contact angle hysteresis and lower mobility. In mixed Wenzel-Cassie states it is possible to have high contact angle and high contact angle hysteresis. However, the hydrophobicity of a textured solid relative to the interacting hydrophobic and hydrophilic components is very important.

In the botanical world, most textured surfaces occur on substrates that are hydrophobic. However, when a hydrophobic fluid replaces the water, a Cassie state can easily be converted to a Wenzel state. This is not always the case, and depends on the vapor pressure and viscosity of the hydrophobic material and how quickly the air trapped in the surface texture can be dissipated.

Various attempts have been made to achieve hydrophobic coatings and surfaces, as follows: U.S. Pat. No. 6,994,045 describes a superhydrophobic coating acting as a substrate for a gaseous lubricant of very low viscosity, has a hierarchical fractal structural of the surface wherein the forms of the first hierarchical level are located at the coating's substrate, and the forms of each successive hierarchical levels are located on the surface of the previous hierarchic level and the forms of individual higher hierarchic levels reiterate the forms of the lower hierarchic levels. U.S. Pat. No. 7,419,615 discloses a method of forming a superhydrophobic material by mixing a hydrophobic material with soluble particles to form a mixture. U.S. Pat. No. 7,887,736 discloses a superhydrophobic surface repeatedly imprinted using a template, so that mass production of a superhydrophobic polymer over a large area can be economically implemented. U.S. Pub. No. 20030147932 discloses a self-cleaning or lotus effect surface that has antifouling properties. U.S. Pub. No. 20060029808 discloses a coating that can remain superhydrophobic after being immersed in water for one week. U.S. Pub. No. 20080015298 discloses a superhydrophobic coating composition. U.S. Pub. No. 20080241512 discloses a method of depositing layers of materials to provide superhydrophilic surface properties, or superhydrophobic surface properties, or combinations of such properties at various locations on a given surface. U.S. Pub. No. 20090011222 discloses a method of applying lotus effect materials as a superhydrophobic protective coating for various system applications, as well as the method of fabricating/preparing lotus effect coatings. U.S. Pub. No. 20090076430 discloses a bandage that includes a material, which can be breathable, having a first surface, and a plurality of superhydrophobic particles attached to the first surface. The material can have a second surface opposite the first surface that is hydrophilic. U.S. Pub. No. 20090227164 discloses a superhydrophobic coating of a nonwoven material is coated with a spongy mesh structure in the micro and nano ranges. U.S. Pub. No. 20100112286 discloses control and switching of liquid droplet states on artificially structured superhydrophobic surfaces. U.S. Pub. No. 20100021692 discloses a method of manufacturing a multiscale (hierarchical) superhydrophobic surface is provided. The method includes texturing a polymer surface at three size scales, in a fractal-like or pseudo fractal-like manner, the lowest scale being nanoscale and the highest microscale. U.S. Pub. No. 20100028604 discloses a superhydrophobic structure comprise a substrate and a hierarchical surface structure disposed on at least one surface of the substrate, wherein the hierarchical surface structure comprises a microstructure comprising a plurality of microasperities disposed in a spaced geometric pattern on at least one surface of the substrate. U.S. Pub. No. 20110077172 discloses a method of localized deposition of a material and includes a superhydrophobic substrate comprising raised surface structures Accordingly, it is an object of the present invention to provide low normal force retractors that create and adherent Cassie and Wenzel states when placed in contact with wet living tissue.

BRIEF SUMMARY

The present disclosure relates to a low normal force retraction device that mechanically retracts surfaces or objects by applying a low-slip microtextured surface. In its simplest embodiments, the retraction device is comprised of one or more arms, jaws or tentacles for retracting an object. These features will be referred to collectively as "arms". The arms in some instances are soft and flexible in a normal direction, and substantially non-distensible in a tangent direction. In other embodiments, one or more arms may be rigid so as to provide a lifting or supportive function, such rigid arms will typically have larger surface area to minimize the normal force per unit surface area during a lifting or retention application.

In other embodiments, the retraction device may consist of a single flexible arm with a microtextured surface that is particularly useful for encircling an object to be retracted. Retraction in this case may include folding one portion of an object over another portion of the same object and holding the folded object in this configuration. When the retraction device is a single flexible arm, it maybe further equipped with other fastening features such as holes or hooks that can be used to anchor the arm to an external anchoring structure. These additional fastening features may be employed in coupling two or more single arm retractors together. These additional fastening features may include without limitation lockable graspers, such as a pliers or forceps.

In the following description, the term "microtextured surface" will be used to mean a surface with a hierarchical structure comprised of microstructures of various spatial scales superimposed to form a single surface with texture on at least two spatial scales. In some embodiments, the microtextured surface comprises three, four or more spatial scales, preferably three or four spatial scales. Examples of microtextured surfaces useful in the present retractors include superhydrophobic surfaces resembling natural rose petal texture. Other examples include surfaces whose contact hysteresis with living tissue is greater than 5 degrees. These surfaces are characterized by the production of a Wenzel-Cassie interface when the microtextured surface comes into contact with a wet or lubricious surface. Other, hierarchical microtextured surfaces include those resembling the surface texture of a lotus leaf, wherein the interface is a Cassie-Baxter type interface.

A microtextured surface may comprise a hybrid of the above-mentioned rose and lotus surface textures wherein one portion is rose-like and other portions are lotus-like, to obtain a "rotus" surface. An arm of the present invention may have a lotus surface on one side and a rose surface on the other side. In the following description, the word "normal force" will be used to mean a force per unit surface area or pressure, wherein the force is orthogonal or normal to the surface area. The surface area typically will refer to the textured surface area of the microtexture arm, and the normal force that force orthogonal to the textured surface of the arm that is applied through contact with an object to be retracted. Accordingly, the normal force can generally be decreased by increasing the surface area of the arm. In some instances it may be useful to be able to alter the surface area of the microtextured arm. Accordingly, the arm may have a corrugated structure that can be made less corrugated to increase the arm's surface area. Other retractors include inflation or distention of the arm. In still other embodiments, the areas of increasing area are decoupled from microstructured areas where the microstructure spatial dimensions are unaltered by the act of increasing the surface area of the arm. The inflation aspect may be used to alter the rigidity of the microtextured arm, or alter its morphology. For example, inflation of two microstructured arms may be configured to create a pincer movement that provides for the alteration of the applied normal forces.

According to different aspects of the invention, microtextured retraction devices according to the invention employ different ways to retain their ability to provide retraction while providing access for other instrumentation to the object to be treated or observed. A microtextured retraction device according to one aspect of the invention, such a retraction device being designated generally as a Type I retraction device, provides retraction by a Wenzel-Cassie effect alone wherein the microtextured surface naturally adheres itself by a hydrophobic interaction with wet surfaces. Type I devices typically have fixed mechanical properties, such as elasticity, rigidity, modulus, and the like. Type II devices include auxiliary components for altering these characteristics and the relation between arms. For example, stiffening an arm or bring two arms to a preferred orientation by inflation. Inflation includes both gaseous and liquid inflation. In gaseous inflation, pressure is controlled, while in liquid inflation, volume is controlled. Composite inflation structures are possible. A first inflation chamber can be formed between two opposing surfaces of a tube-shape microtextured arm, wherein bridging structures between opposing surfaces maintains an approximately flat tape-shaped microtextured arm under inflation. An additional inflatable chamber, which forms an inner smaller tubular structure inside the first chamber of the microtextured arm. Under inflation, this second chamber may provide a preferred curved structure to the microtextured arm. The second inflatable chamber is normally inflated after the main inflatable chamber of the retraction device has been inflated, and the retraction device has produced its desired retraction effect. Such an additional inflatable chamber is smaller and less powerful than the main inflatable chamber. Inflating the additional chamber alone would not always produce sufficient force to provide the desired retraction of the organ. However, the inflated additional chamber provides enough force to maintain an object that has been retracted by the more powerful main inflatable chamber in its retracted position. The additional inflatable chamber is thus able to maintain the retraction effect of the retraction device after the retraction effect of the main inflatable chamber has been destroyed by piercing an aperture in the envelope of the main chamber to provide access to the object to be treated.

A Type I or a Type II retraction device according to the invention may be provided, according to a further aspect of the invention, with tabs attached to the surfaces of the microtextured arms of the device. The tabs are gripped with a suitable gripping tool to adjust the position and orientation of the retraction device relative to the tissue to be treated.

According to a further aspect of the invention, a Type I or a Type II retraction device may be provided, when in its first state prior to actuation, with markings on its surface to aid proper orientation prior to actuation or similar markings intended to indicate regions of different surface texture. According to a further aspect of the invention, a Type I or a Type II retraction device can possess a corrugated surface wherein one configuration of the corrugation provides an adhesive Wenzel-Cassie surface and in another configuration of the corrugation provides a low friction Cassie-Baxter surface. This feature may be used to release a retracted object in a manner that would reduce potential damage to the object if release was attempted while in the Wenzel-Cassie state. For example, a Type I device could be in a first adhesive state and subsequently made nonadhesive by irreversibly deforming the microstructure arm by applying a tangent stretching motion to the microtextured arm. In a Type II device, the same can be achieved reversibly by an inflation action.

According to a further aspect of the invention, in a retraction device according to the invention, an arm may be incorporated with a suction tube for removing free liquid at the retraction site. Alternatively, a microstructured arm may be fitted with an attachment for such a suction tube. In the case of retraction during a surgical procedure, suction aspect is connected to the operating room suction line and allows continuous or intermittent drainage of fluid that collects in the bottom of a surgical cavity created by the retraction device during laparoscopic surgery.

DETAILED DESCRIPTION OF THE INVENTION

Figure 1:
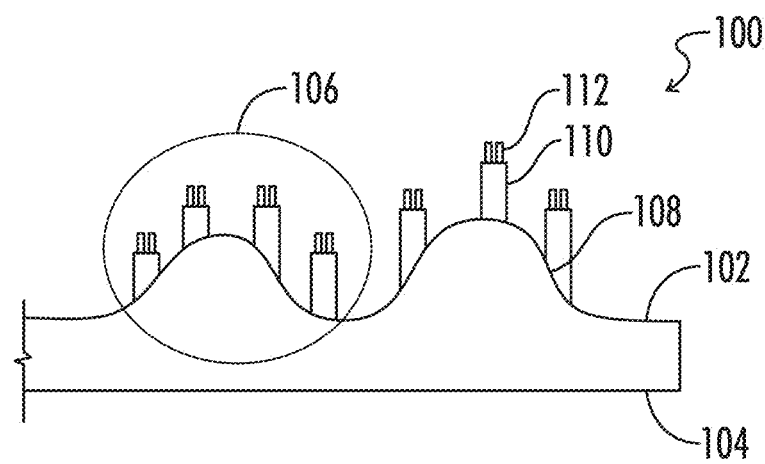
FIG. 1 is a cross-sectional view of a superhydrophobic Wenzel-Cassie surface embodiment of the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that must be included in all embodiments, unless otherwise stated.

Type I Devices

FIG. 1 shows a vertical view of a first embodiment 100 of a retraction device according to the invention. This type of retraction device is essentially fixed in its mechanical and geometrical aspects and will be designated as a Type I retraction device. The retraction device is shown in its flat condition, and it is understood that the device has sufficient flexibility that it can be made to conform to the surface of an object to be retracted. The retraction device 100 comprises a first side 102 and a second side 104. Retraction device 100 is made of a relatively inelastic and tough film of a plastic such as polypropylene, polyethylene, or polyurethane. The preferred material is a polyethylene and nylon composite. The thickness of the retraction device 100 is typically from 0.5 to 5 mm. A surface texture 106 is comprised of large scale structure 108, intermediate scale structure 110, and microscale structure 112. The microscale structure 112 is superimposed on intermediate scale structure 110, and this combination is superimposed on large scale structure 108. Large scale structure 108 has a characteristic dimension between 100 and 1000 microns. Intermediate scale structure 110 has a characteristic dimension between 25 and 100 microns. Microscale structure 112 has characteristic dimension between 1 and 25 microns.

Generally, the size and shape of the retraction devices are application dependent. For example, in a surgical application, the size of retraction devices according to the invention can range from about 2" (50 mm) long by about 0.5" (12 mm) wide, for use inside the pericardium, to 10"14"(250- 350 mm) long by 2"8" (50-200 mm) wide, for use in the abdominal cavity. The size of retraction device required for a given application depends on the application and the size of the patient.

Type II Retraction Devices

The basic embodiment of a Type II retraction device includes a single inflation chamber. In alternative embodiments, a single chamber can be divided into a plurality of subchambers. The subchambers are isolated from one another, so that if one or more of them is accidentally punctured while the retraction device is in use, deflation of all of the retraction device can be avoided. Each subchamber can be equipped with its own additional inflation tube. Alternatively, each subchamber can be connected to an inflation manifold through a nonreturn valve. The manifold arrangement requires that each subchamber be individually deflated in preparation for withdrawing the retraction device from the body at the end of the treatment procedure. The main advantage of these subchambers, intercommunicating or separate, is to define a preferred geometry under inflation.

Figure 2:
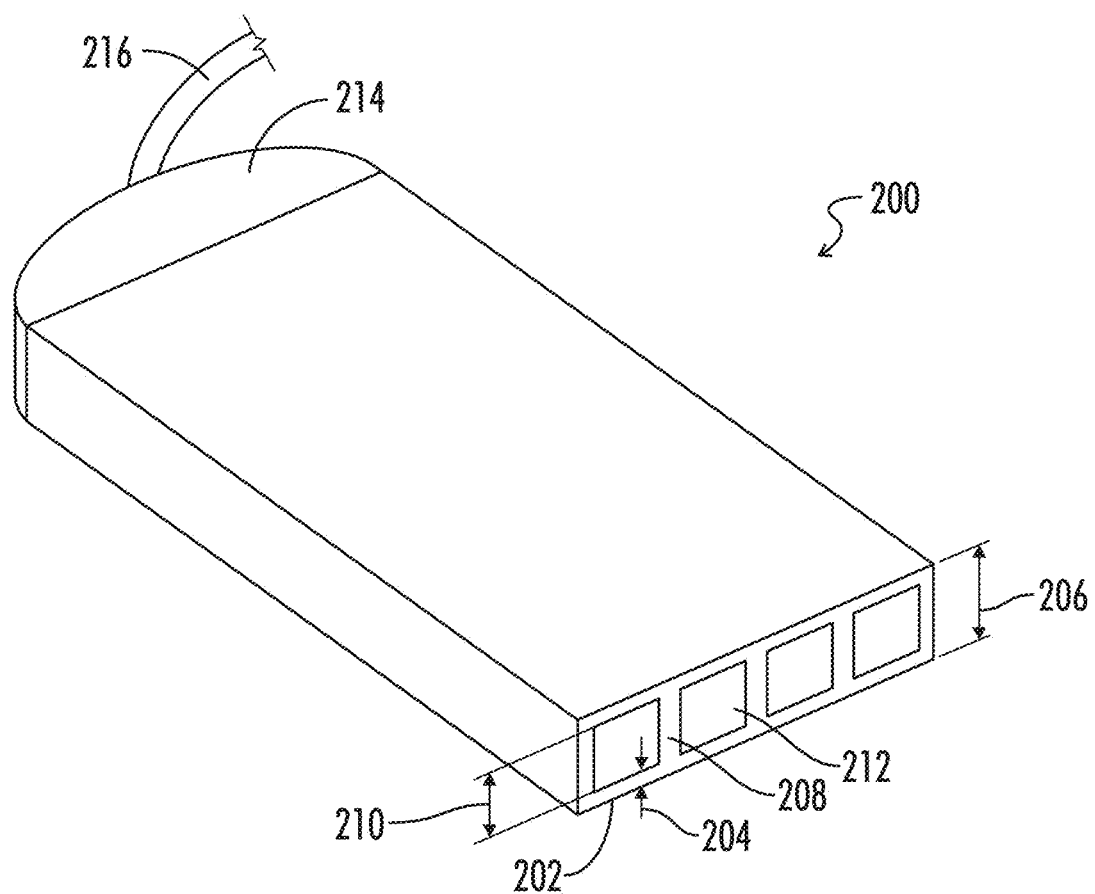
FIG. 2 is a perspective view of a tape-like Type II inflatable retraction device according to a second embodiment of the invention.

FIG. 2 is a perspective view of a Type II device 200 with multiple inflation chambers. The main envelope 202 is made of a relatively inelastic and tough film of a plastic such as polypropylene, polyethylene, or polyurethane. A preferred material for the main envelope is a polyethylene and nylon composite. The wall thickness 204 of the main envelope 202 is typically from 0.5 to 5 mils (13 to 130 microns). When inflated, the device thickness 206 of the microstructured arm 200 is between 1 mm and 5 mm. The device thickness 206 is limited by height 210 of inelastic members 208 that form the individual subchambers 212. Subchambers 212 run to a manifold 214. Air or liquid pressure is delivered by tube 216. The delivery tube 216 can be small and flexible with diameter 218 in the range 1 mm to 5 mm. The main inflation tube 216 allows an inflation gas to pass into and out of the subchambers 212. An inflation gas is typically air, nitrogen or carbon dioxide, although other suitable gases may be used. An inflation liquid is typically physiologic saline. Typical inflation gas pressures are in the range 0.3 to 0.7 psi (0.21 to 0.48 Pa), the preferred pressure being 0.5 psi (0.35 kPa). Once the device 200 is fully inflated, the inflation gas pressure can be reduced to about 0.3 psi (0.21 kPa).

Additional Features to Type I and Type II Devices

Suction Aspect

Figure 3:
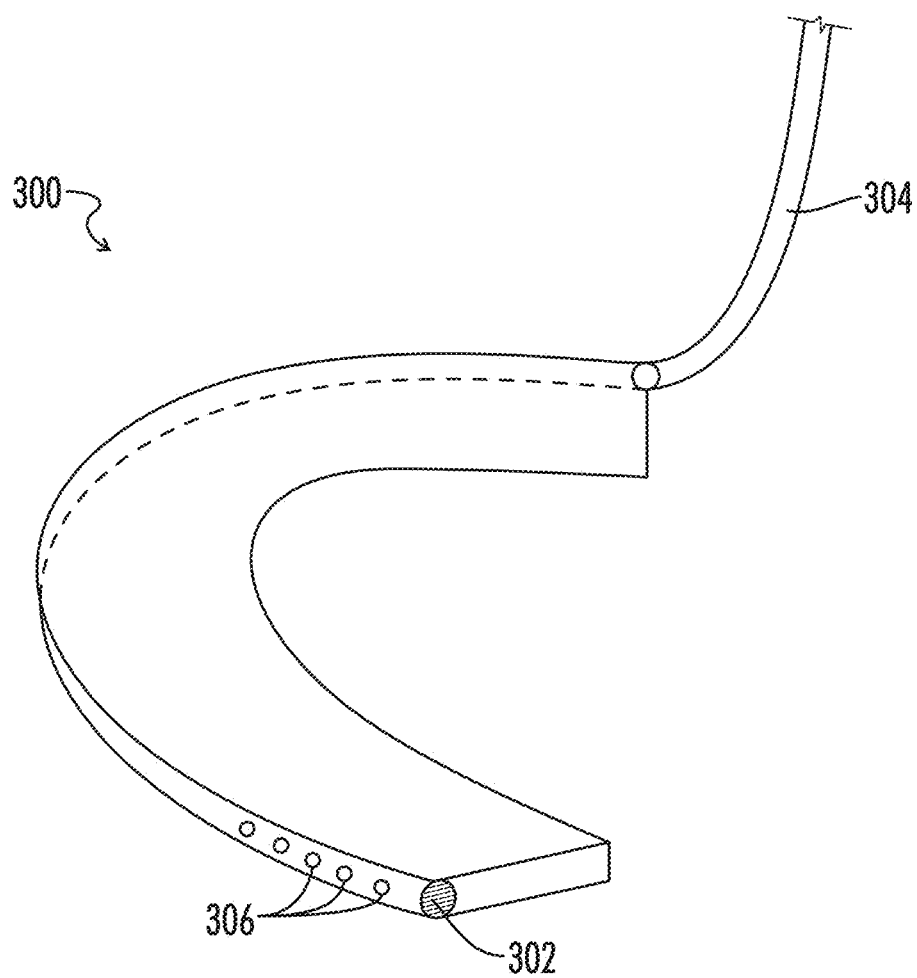
FIG. 3 is a perspective view of a Type I retraction device fitted with a suction means according to a third embodiment of the invention.

According to a further aspect of the invention, a retraction device according to the invention may be fitted with a tubular suction portion on the part of the retraction device that is lowermost when the retraction device is deployed in a cavity with liquid present. FIG. 3 shows a Type I device with the suction feature attached. The suction portion of this aspect of the invention can be used with Type I and Type II retraction devices. Irrigation is often used when retraction is applied to a cavity environment. The irrigation is used to clear away debris. In the case of a surgical applications, the debris consists of blood and clotted elements. This fluid collects in the bottom of the cavity in the body created by the retraction device and needs to be cleared away. The suction portion 302 is integral to microstructured retractor 300. The bottom of the retraction device 300 is connected to a suction line 302 and removes such fluid during the treatment procedure, keeping the cavity clear of accumulated fluids. In the example shown, the suction portion 302 is a tubular appendage attached to the lowermost extremity of the retraction device. The suction portion can be made of the polyethylenenylon composite that is the preferred material for the main body of the retraction device. This material is sufficiently resilient that a tubular structure made from it can retain its open cross section under a low vacuum. One end of the suction portion 302 is closed; the other is connected to a thin wall polyethylene tube 304 that runs up the side of the retraction device to exit the body through the same incision through which the retraction device is delivered. Suction is delivered to the operative site through holes 306.

Curved Retraction Devices

Curvature can be formed within a tape like microstructured retractor arm. For example, the curvature may have a radius of curvature that is substantially less than the length of the retractor such that when in the relaxed state the arm curls on itself at least 1 time. The preformed radius of curvature along with the stiffness of the materials used determine the normal force when the object enclosed in the retractor is larger than the radius of curvature. In most cases, the normal force is proportional to the ratio of the object's diameter to the retractors radius of curvature.

Figure 4:
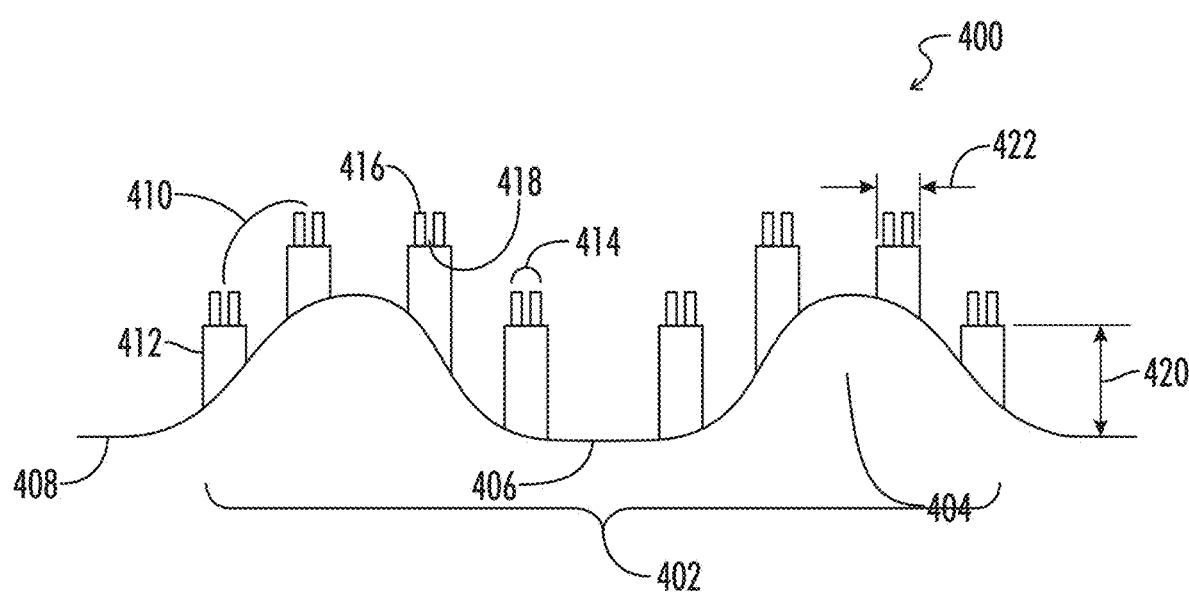
FIG. 4 depicts a microstructured surface useful for a low normal force retractor.

Referring to FIG. 4, generally a surface for an low normal force retractor surface 400 of the present invention possesses a hierarchical surface comprised of a large scale structure 402 with a plurality of protuberances 404 and depressions 406 disposed in a geometric pattern on at least one surface of a substrate 408, and a medium scale structure 410 disposed on at least one surface of the large scale level structure 402 is comprised of protuberances 412. The small scale structure 414 is similarly comprised of protuberances 416 and depressions 418 disposed on the medium scale structure 410. The large scale protuberances 404 should be high enough so that a hydrophilic component of a hydrophobic/hydrophilic contact mixture does not touch the large scale depressions between adjacent protuberances 404. In the embodiment of FIG. 4, the large scale protuberances 404 may comprise a height H of between about 25 to about 1000 microns and a diameter D of between about 25 to about 2000 microns, wherein the fraction of the surface area of the substrate 408 covered by the protuberances 404 may range from between about 0.1 to about 1.0. The medium scale protuberances 412 may comprise a height 420 of between 5 to about 25 microns and a diameter 422 of between 5 to about 50 microns, wherein the fraction of the surface area of the substrate 408 covered by the protuberances 412 may range from between about 0.1 to about 0.9. The small scale structure 414 may be disposed primarily on the medium scale structure 412. The arrangement of hierarchical structures may be geometric and describable generally with a mathematical equation. Alternatively, the hierarchical structures may be randomly disposed, possibly with varying pitch, which is more typical of natural structures. The arrangement of hierarchical structure can generally be described by a fractal dimension.

A fractal dimension is a statistical quantity that gives an indication of how completely a collection of structures appears to fill space, in the present case a plane, as one examines that structure on a multiplicity of spatial scales. Specifying a fractal dimension, which is statistical in nature, does not necessarily indicate that the hierarchical structure is well defined by a mathematical equation. Generally, a random arrangement of structures within a specific scale possesses a higher fractal dimension than one in which the structure is mathematically described at all points on a surface. Thus, a random structure may possess an advantage in the aspect that an adhesive surface of the present invention has greater utility when interacting with a natural surface. A higher fractal dimension within a specific spatial scale may be achieved by applying to a substrate multiple pitch arrangements. The protuberances and depressions may be locally scaled with respect to the local pitch. Accordingly, the pitch may vary within a scale structure. In the practical realization of higher fractal dimension structures, the variation of the pitch may be describable by a mathematical equation, for example, a sinusoidal variation of pitch, which would have utility in mimicking natural surfaces.

Generally, structures can be described as sharp-edged or rounded, and this feature is not typically captured by a fractal dimension. Another structural aspect not addressed by the above descriptive parameters is the degree of communication between structures. By communication, it is meant that a structure, such as a protuberance or a depression, has a spatial extent greater than the pitch. For example, a valley surrounding a protuberance may be connected to another valley surrounding another protuberance, thus the depressions are said to be communicating whereas the protuberances are not. The communication may range from 1 to about 1000, more particularly the communication may extend over the entire surface of the substrate. These structures are constructed with the purpose of creating Wenzel and Cassie states, on a multiplicity of scales, when the low normal force retractor of the present invention comes in contact with a hydrophobic/hydrophilic contact mixture.

A scale of interaction is defined by the surface texture of the present low normal force retractor, and is typically hierarchical, and characterized by at least two spatial scales, one on the order of micrometers (microns) and another on the order of 100s of microns. The surface texture may induce one state with a large difference between preceding and receding contact angles (contact angle hysteresis), or alternatively another state with a small contact angle hysteresis. States of interest are known respectively as Wenzel and Cassie states. Each of the hierarchical spatial scales may induce separately a Wenzel or Cassie state, such that combinations are possible on a multiplicity of spatial scales.

These states are phenomena between hydrophobic and hydrophilic components of a mixture residing at a textured surface interface. In the Cassie state the adherent textile is resistant to hydrophobic debris adhesion, for example oil in an oil water mixture. In the Wenzel state the implant is reversibly adherent to a hydrophilic surface, for example a wet or ice surface. In hybrid Cassie-Wenzel states, where one texture scale is Wenzel and the other is Cassie, the retractor can be both localizing to a wet surface and resistant to hydrophobic contaminants such as fats.

The interaction of a solid textured surface with water in a gaseous environment is described by the Cassie-Baxter model. In this model, air is trapped in the microgrooves of a textured surface and water droplets rest on a compound surface comprising air and the tops of microprotrusions. The importance of a fractal dimension between multiple scales of texture is well recognized and many approaches have been based on the fractal contribution, i.e., the dimensional relationship between different scales of texture.

However, regardless of the material (organic or inorganic) used and geometric structure of the surface texture (particles, rod arrays, or pores), multiple scales of texture in combination with low surface energy has been required to obtain the so called superhydrophobic surfaces. Superhydrophobicity is variously reported as a material exhibiting a contact angle with water that is greater than contact angles achievable with smooth but strongly hydrophobic materials. The consensus for the minimum contact angle for a superhydrophobic substance is 150 degrees, so in this context some of the embodiments of the present invention are not strictly superhydrophobic, although this option is not excluded The reason for this is that a Wenzel-Cassie state lies in its hydrophobicity between nontextured surfaces and surface that generate a Cassie-Baxter interface. In optimizing the adherence of the textiles of the present invention superhydrophobicity is just one aspect of a number of interesting texture controlled mechanisms, and in this context the contact angle is less important than the contact angle hysteresis.

It is known in the art that the transition to the Wenzel state can be discouraged by the use of sharp cornered features in the plane of the surface. However, the occurrence of sharp cornered structures in natural structures, such as rose petals, is less common. Natural structures tend to possess rounded surface features, especially radiused or filleted corners. In nature, resistance to conversion to a Wenzel state seems to involve the creation of involute rounded structures rather than sharp edges. By involute it is meant concavity oriented in a line not orthogonal to the substrate surface. Such structures are difficult to create by an etching or casting method, but can readily be created by an embossing method that entails folding of a structure.

Similarly, the Wenzel state can be discouraged by the use of curving communications between structures as opposed to straight line communication. In most cases, higher hydrophobicity equates with lower propensity for a Wenzel transition. The hydrophobicity of a surface is enhanced by the placement of exterior corners around depressions. In some embodiments, this is achieved by the creation of additional pairs of adjacent depression walls that project into and are joined at the interior of the depression. In some embodiments this is achieved by designing an ordered array of depressions of a first hierarchy (examples: triangular, rectangular, pentagonal, or hexagonal shapes, regular or irregular; and further polygonal shapes defined generally by straight line segments).

A second feature of smaller size and different hierarchical order is then superimposed on the depression wall of the first pattern. The method employed in creating such a structure may involve first emboss a large scale structure and then secondarily emboss additional smaller scale structure, preferably smaller scale structure embossed on larger scale structures.

Water possesses a dipole structure which makes it attractive to any other substance that is charged. Molecules with a charge surplus localized at a specific location on the molecule renders that molecule hydrophilic. In the case of polymers, the charges can associate, and the bulk substance and possess a macroscopic charge. And in such macroscopic assemblages, such materials are strongly water attractive. And when those macroscopic charge localities are associated with surface texture, than a substance becomes superhydrophilic. The term superhydrophilic has various meanings in the literature, and in many cases simply refers to the rendering of a substance more hydrophilic, or a decrease in contact angle relative to a flat surface of the same substance. Here, it is meant the accentuation of surface charge and surface energy such that water is always bonded to the substrate surface, even though any particular water molecule may have a short residence time on the polymer surface. This has a commercial advantage in that the adherent surface of the low normal force retractor is both shielded from contaminating debris and also is self-washing due to the stochastic attachment/detachment of water molecules from the surface. The methods of manufacture of textured surfaces low normal force retractors of the present invention include lithography, casting, extrusion/embossing, and any of several methods for transferring a texture to a surface. Methods for forming such hierarchical microstructured surfaces are described in U.S. application Ser. No. 14/802,632, which is hereby incorporated by reference in its entirety.

A preferred method is embossing, where a polymeric substance is heated to a molten state and passed through dual rollers, at least one of which contains a negative image of the desired embossed structure. A small scale texture is embossed on a planar sheet. This embossed planar sheet is heated to a malleable but not fluid state and passed through dual rollers possessing a medium scale texture which impresses an inverse image. This process can be repeated multiple times. The medium scale texture is large relative to the small scale texture, thus the impression of the medium scale texture folds the small scale texture, making possible involute structures which would ordinarily not be possible with a lithography or casting method.

The low normal force retractors of the present invention have three or more levels of textures assembled in a manner to yield a high surface area while maintaining a minimum spacing between textures to allow for liquid flow and penetration to promote in the first instance surface washing and in the second instance surface adhesion; and while maintaining a minimum structural strength obtained by keeping height to width aspect ratio of all features below a critical level at which material strength is exceeded.

Figure 5:
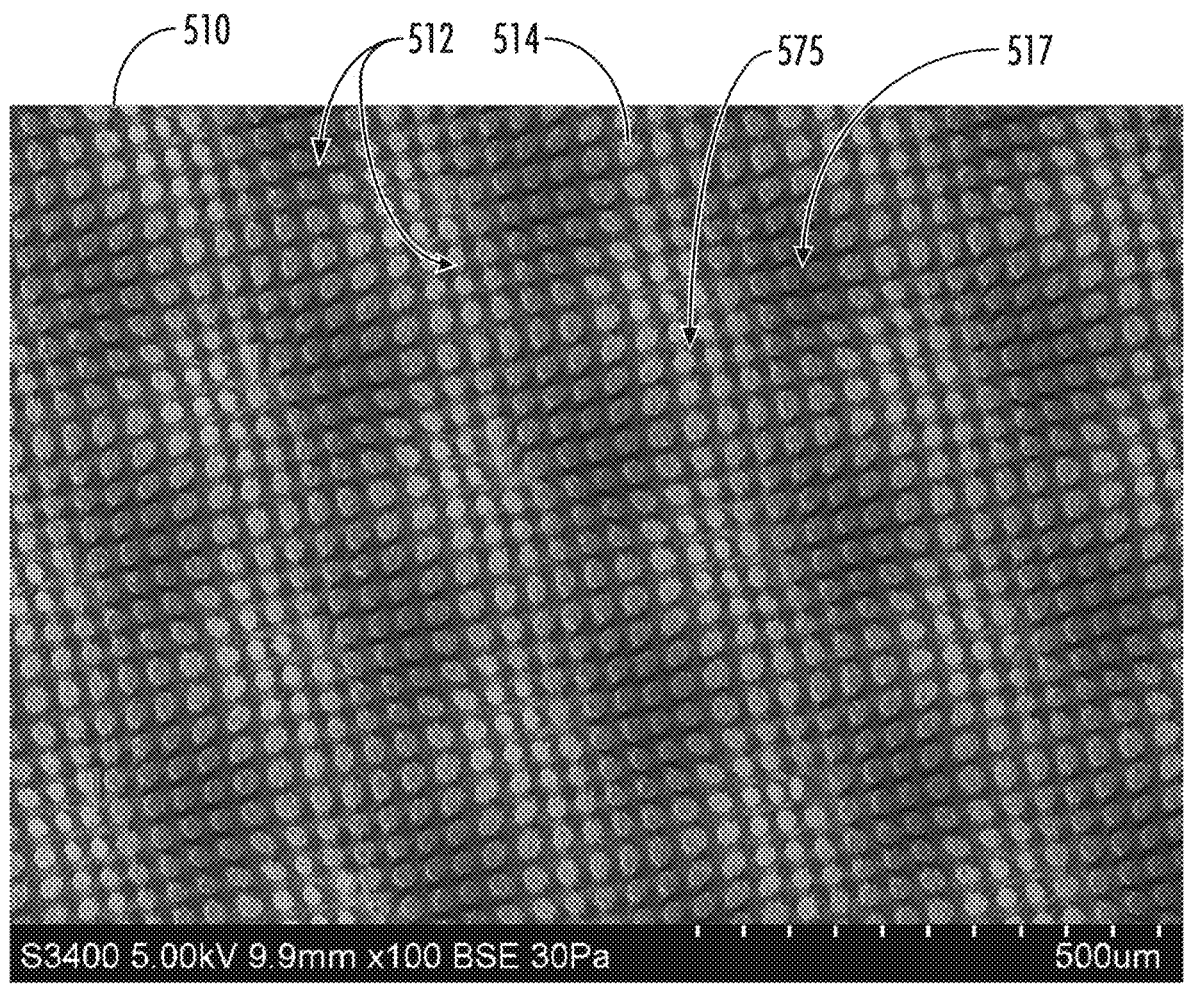
FIG. 5 depicts a first embodiment of a low normal force retractor surface.

Referring to FIG. 5, a first embodiment of a low normal force retractor arrangement 500 on a textile surface according to the present invention is shown comprising a substrate, designated generally as 510. In the illustrated embodiment, substrate 510 has a sinusoidal waveform comprising a series of rounded peaks and valleys that produce a continuously curving surface across at least a portion of substrate 510. The sinusoidal waveform of substrate 510 defines a first set of large scale features, designated generally as 512, while a second set of microfeatures, 514 are disposed on the large scale features.

In FIG. 5, substrate 510 is constructed and arranged to focus on a series of rounded knobs forming peaks 515 projected upwardly from the surface with associated valleys 517 disposed between peaks 515.

Figure 6:
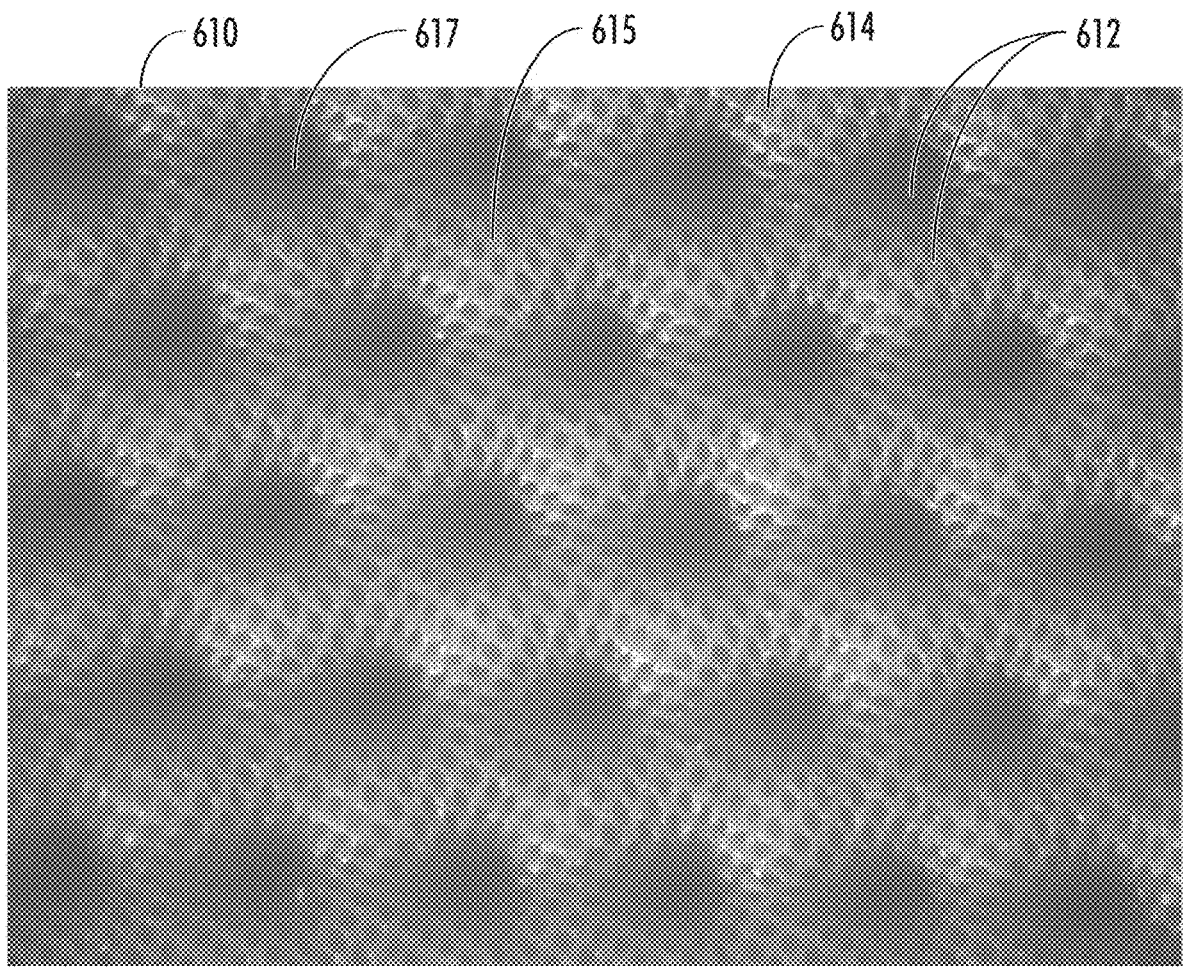
FIG. 6 depicts a second embodiment of having an inverse surface.
Figure 7A:
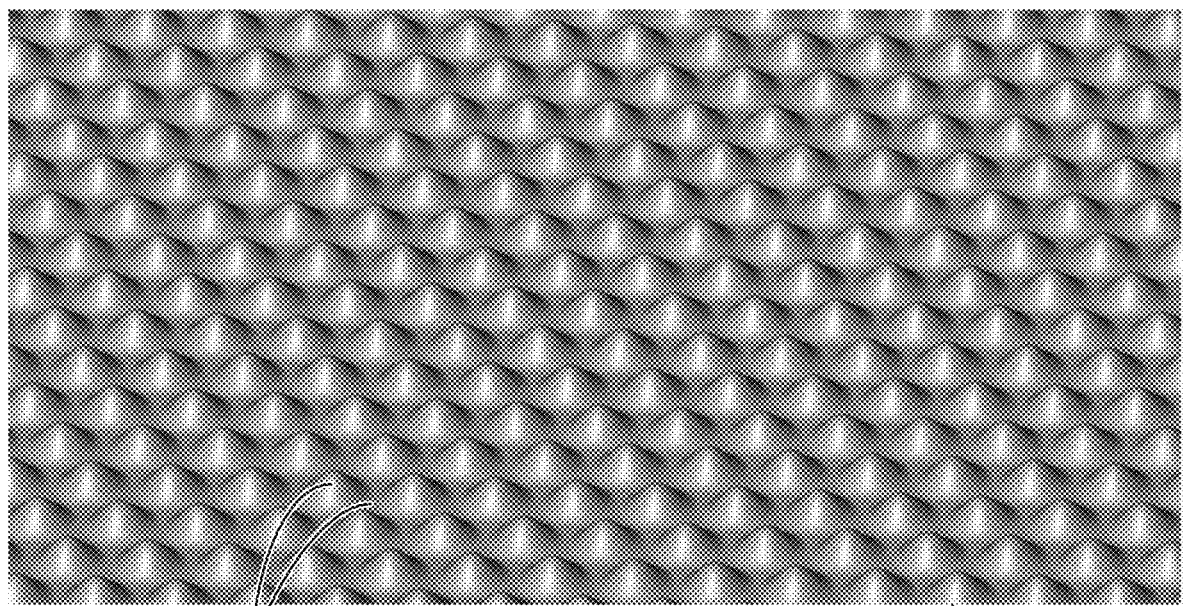
FIGS. 7A-7D depict a selection of substrates 710 having various sinusoidal waveform patterns that provide alternative curved surface texture features across substrate 710
Figure 7B:
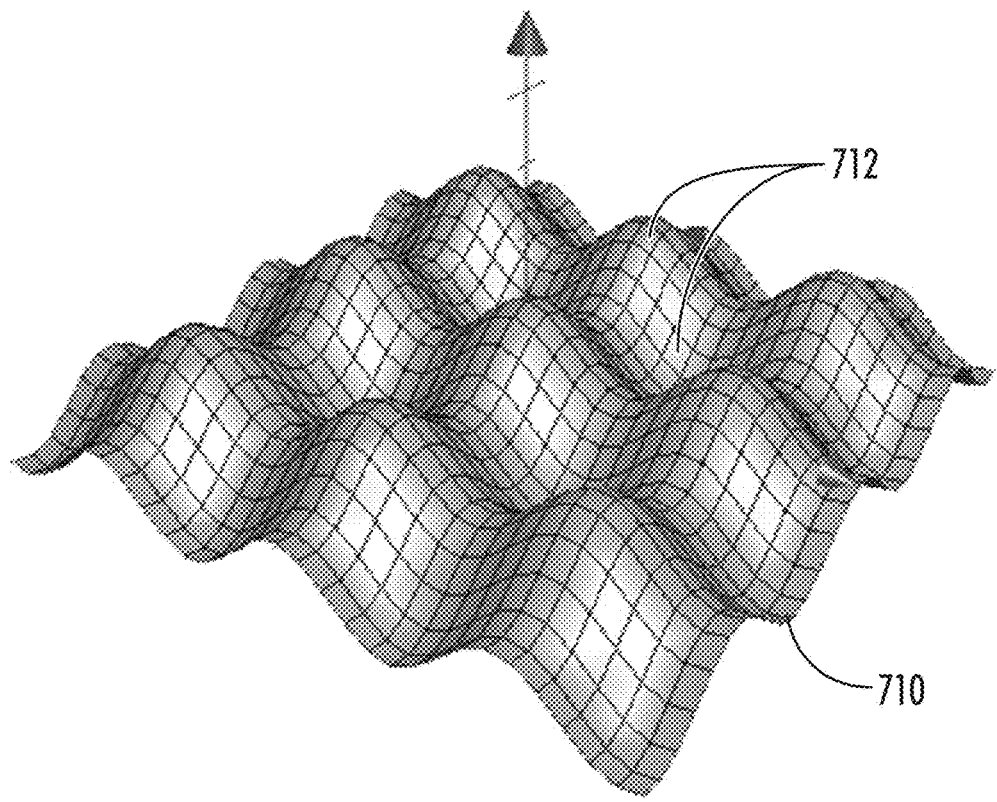
Figure 7C:
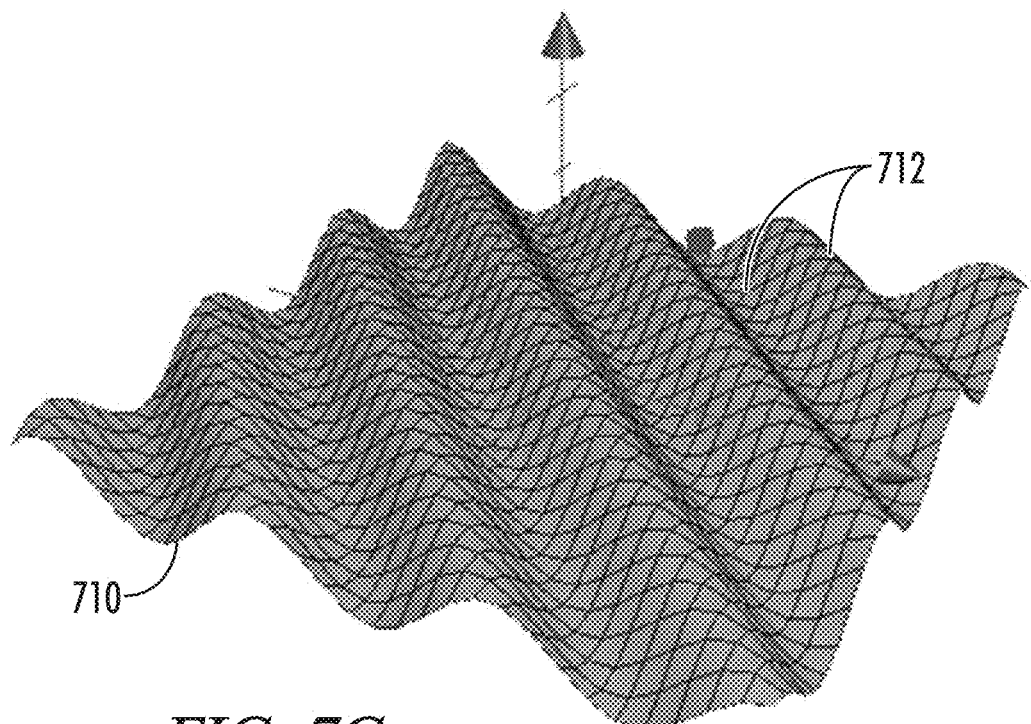
Figure 7D:
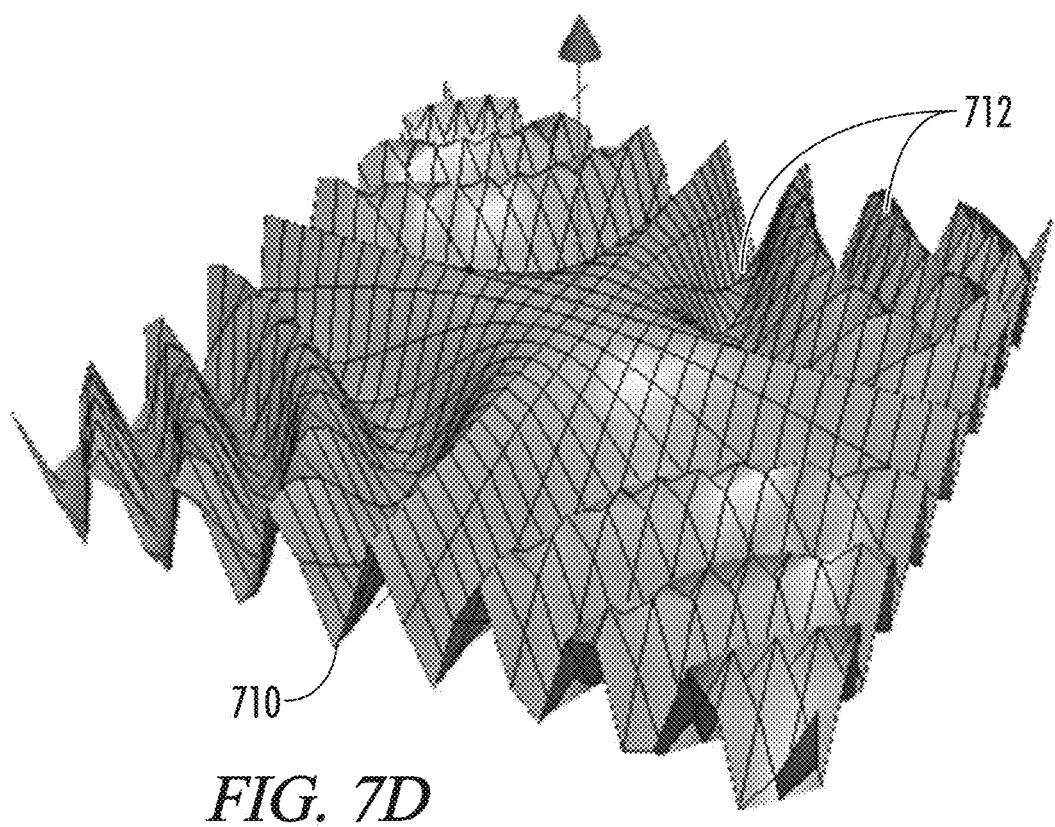

In a second embodiment shown in FIG. 6, the inverse arrangement is shown in which substrate 610 is constructed and arranged to focus on a series of rounded cavities forming valleys 617 extending inwardly into substrate 610 as the dominant feature with the associated peaks 615 disposed between valleys 617, and 614 indicates a second set of microfeatures. In both embodiments, the surface of substrate 610 is continuously curving throughout sinusoidal waveform pattern area.

According the present invention, the term sinusoidal waveform as used herein refers to a surface having a repetitive oscillation of rounded, nonflat curvature described by mathematical formulas incorporating trigonometric functions sine, cosine, tangent or exponential and power series functions. These mathematical formulas are used in computer aided design and computer aided manufacturing software to create texture surfaces using rapid prototyping, milling, electrical discharge machining or similar techniques to create a polymer or metal surface with the sinusoidal waveform texture features. The advantage of using mathematical formulas is that large numbers of rounded, nonflat features can be created rapidly in computer aided design and computer aided manufacturing software. Texture features of this type cannot be created using lithographic techniques.

Figure 8:
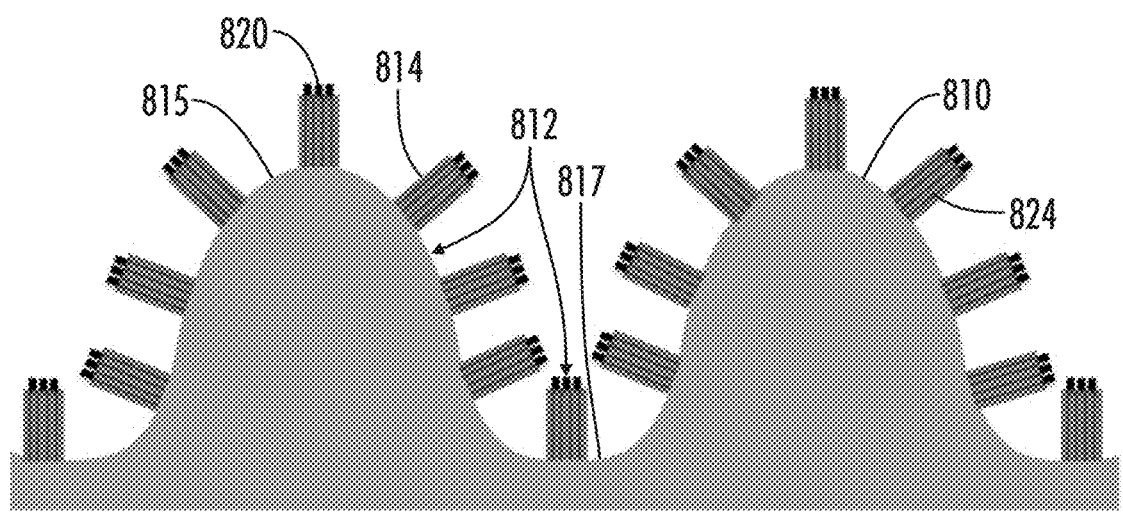
FIG. 8 depicts a side view of an embodiment of the microstructured surface on a substrate according to the present disclosure having a second set of features disposed on the surface of the substrate.
Figure 9:
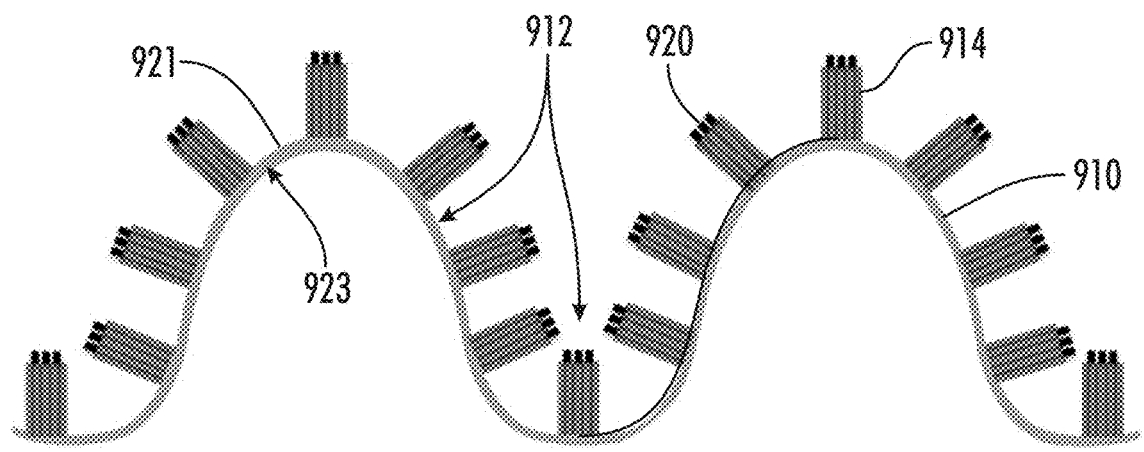
FIG. 9 depicts a side view of another embodiment of the microstructured surface on a thin substrate according to the present disclosure.

Referring to FIGS. 7A-7D, a selection of substrates 710 are shown having various sinusoidal waveform patterns that provide alternative curved surface texture features across substrate 710. These embodiments are for illustrative purposes only as example embodiments of substrate 710 and are not limiting of the present invention and the term sinusoidal waveform as used herein. According to the present invention, first set of texture features 712 includes dimensions selected from a size within a range of about 100 microns to about 1000 microns. More specifically as will be detailed herein below, in a preferred embodiment, the sinusoidal waveform is arranged so that first set of texture features 712 has sinusoidal rounded cavities of 750 microns, a pitch of 750 microns, and a depth of about 240 to 500 microns. This arrangement of the substrate is intended to promote an adhesive Wenzel-Cassie state with a hydrophobic/hydrophilic contact mixture. Referring to FIGS. 8 and 9, a second set of texture features 814 and 914 are disposed on the surface of substrate 810 and 910. In one embodiment, second set of texture features 814 is molded on first set of texture features 812 and 912 of substrate 810 and 910, respectively. As detailed herein below, in a preferred embodiment, substrate 810 or 910 is a compression molded polymeric material in which first and second sets of texture features 812, 814 and 912, 914 are formed on substrates 810 and 910, respectively, during a single molding step. First and second sets of texture features 812, 814 cooperate to increase the surface area and affect at least one of adhesion, friction, hydrophilicity and hydrophobicity of substrate 810 and 910. Preferably, the compression molded polymeric material forming substrate 810 is an environmentally durable polymer. In one embodiment, substrate 810 or 910 comprises polyethylenenylon copolymer. In the illustrated embodiments, second set of microstructures 814 or 914 is selected from the group consisting of microstructured projections and microstructured cavities, and combinations thereof. In the illustrated embodiment in FIG. 6, second set of texture features 614 comprise microstructured cavities extending downwardly into substrate 610.

In the illustrated embodiments of FIGS. 8-11, second set of texture features 814, 914, 1014 and 1114 comprise microstructured projections extending upwardly from substrate 810, 910, 1010, and 110, respectively. Preferably, in the illustrated embodiments of FIGS. 8-11, the microstructured projections of said second set of texture features 814, 914, 1014 and 1114 comprise generally cylindrical pillars.

Preferably, in the illustrated embodiment of FIG. 6, the microstructured cavities of second set of texture features 614 comprise generally cylindrical recesses.

Referring to FIG. 9, in one embodiment in which substrate 910 is a thin film substrate and has operable opposing top and bottom surfaces, first set of texture features 912 disposed on a top surface 921 of substrate 910 form a complementary shape on a bottom surface 923 of substrate 910 so that a rounded peak on top surface 921 forms a rounded valley on bottom surface 923 and the rounded valley on top surface 921 forms a rounded peak on bottom surface 923.

Again referring to FIG. 9, in an embodiment in which substrate 910 is a thin film substrate and has operable opposing top and bottom surfaces, second set of texture features 914 includes a series of microstructured projections on one of top surface 921 and bottom surface 923 of substrate 910, which then define a series of complementary microstructured cavities on the other of said top surface and said bottom surface 921, 923.

Likewise, in an embodiment in which second set of texture features 914 comprises microstructured cavities which project downwardly through substrate 910 from a top surface 921, they form complementary microstructured projections on the opposing bottom.

Referring to FIGS. 5, 8 and 9, in the illustrated embodiments, second set of texture features 514, 814 and 914 include at least a portion of texture features that extend along an axis normal to the curve of the sinusoidal waveform of substrate 510, 810 and 910 at a given point for the individual microstructure. In this way, the second set of texture features follow the curvature of first set of texture features 512, 812 and 912.

According to the present invention, second set of texture features includes dimensions selected from a size within a range of about 10 microns to about 100 microns. Further, second set of texture features preferably have a height to width aspect ratio of less than 5, and a minimum spacing of 1 micron between each texture feature of said second set of texture features to maintain structural strength while allowing for liquid flow and penetration between the individual microstructures comprising second set of texture features.

Referring again to FIGS. 8-11, a third set of texture features 820, 920, 1020 and 1120 may also be disposed on substrate 810, 910, 1010 and 1110, respectively. Preferably, third set of texture features 820 is selected from the group consisting of microstructured projections and microstructured cavities, and combinations hereof. In one embodiment, the microstructured projections of third set of texture features 820, 920, 1020 and 1120 comprise generally cylindrical pillars.

Referring to FIG. 6, in one embodiment, the microstructured cavities of third set of texture features 620 comprise generally cylindrical recesses. Preferably, third set of texture features 620 are compression molded simultaneously with first and second sets of texture features 612, 614. In a further preferred embodiment, third set of texture features 620 have a height to width aspect ratio of less than 5, and a minimum spacing of 1 micron between each texture feature of third set of texture features 620 to maintain structural strength while allowing for liquid flow and penetration between said third set of texture features. The aspect ratio is smaller when devices are made of lower strength materials and larger when made from stronger materials. The spacing between features is smaller for less viscous liquids and larger for more viscous Referring to FIGS. 5, 8, 9, third set of texture features 520, 820 and 920 include at least a portion of texture features that extend along an axis normal to the curve of the sinusoidal waveform of substrate 10. For purposes of the present invention in which the second and third sets of texture features extend along an axis normal to the curve of the sinusoidal waveform, the normal line to a curve is the line that is perpendicular to the tangent of the curve at a particular point. In the illustrated embodiments, second set of texture features 514, 814 and 914 is smaller than first set of texture features 512, 812 and 912, respectively, and third set of texture features 520, 820 and 920 is smaller than second set of texture features 514, 814 and 914, respectively According to the present invention, the third set of texture features includes dimensions selected from a size within a range of about 1 micron to about 10.

Referring to FIGS. 5 and 8-11, in one embodiment, third set of texture features 520, 820 and 920 are disposed on an end surface 522, 822 and 922 of second set of texture features 514, 814 and 914. In a further advantageous embodiment, third set of texture features 520, 820 and 920 are disposed on first set of texture features 12 between second set of texture features 14. In a further advantageous embodiment, third set of texture features 20 are disposed on an end surface 22 of second set of texture features 14, as well as, disposed on first set of texture features 12 between second set of texture features 14. 30

Figure 10:
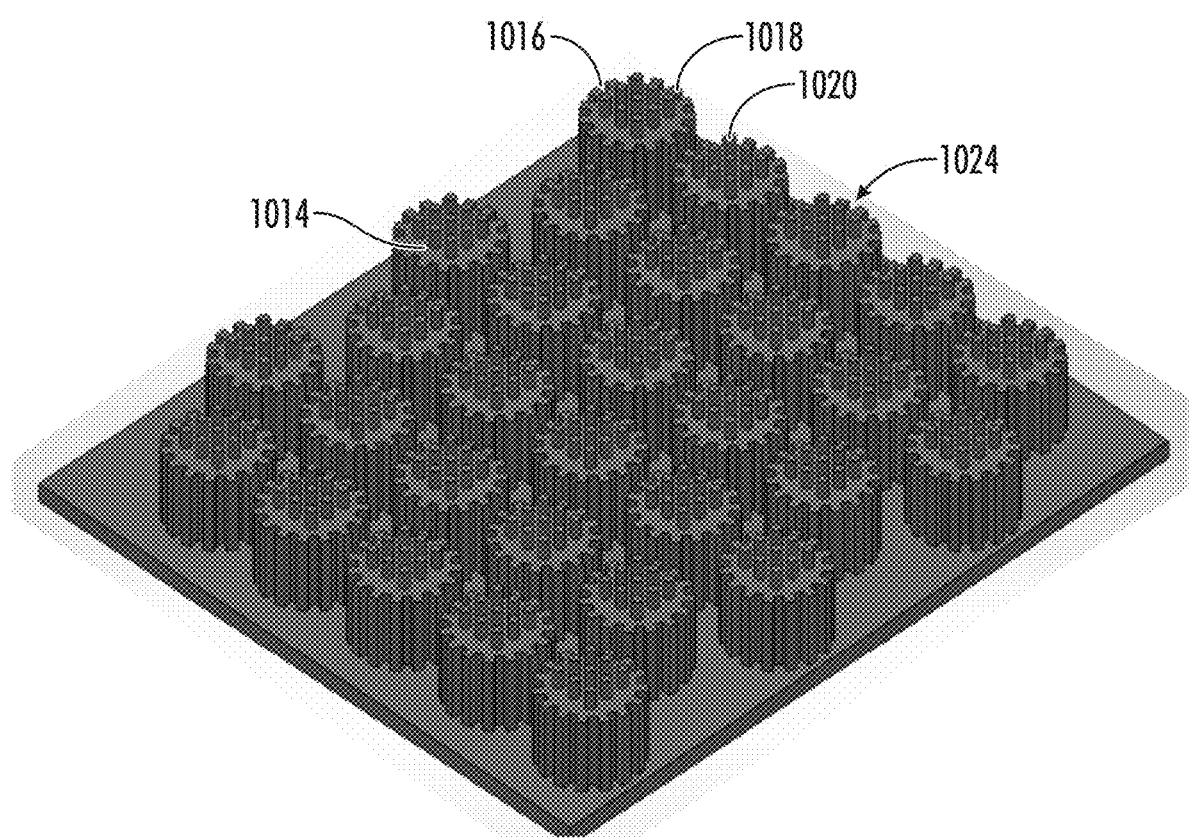
FIG. 10 depicts a perspective view of a microstructured surface having a fourth set of microfeatures.
Figure 11:
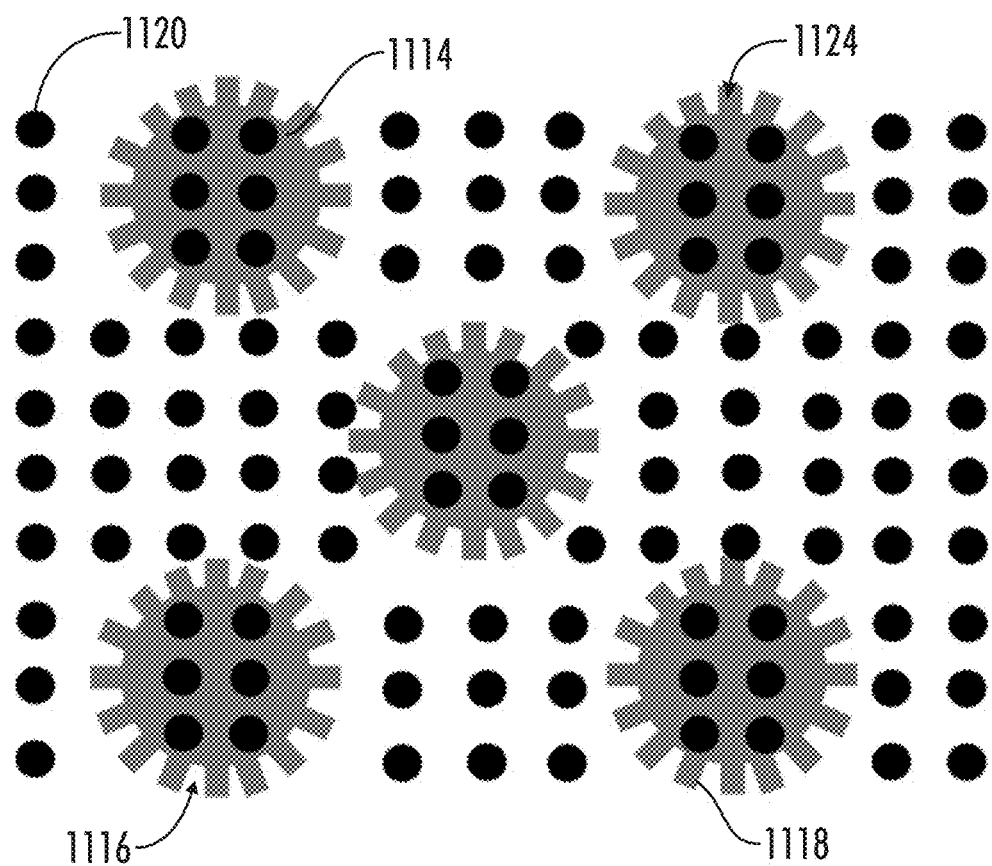
FIG. 11 depicts a schematic top view of a microstructured surface having a fourth set sets of microfeatures.

Referring to FIGS. 10 and 11, a fourth set of texture features 1024 and 1124 may be disposed on side surfaces of second set of texture features 1014 and 1114, respectively. Fourth set of texture features 1024 and 1124 is selected from the group consisting of flutes 1016, 1116 and ribs 1018, 1118 and combinations thereof. In the illustrated embodiments, flutes (1016, 1116) and ribs (1018, 1118) run vertically along the height of the side surfaces on the outside circumference of each microstructure comprising said second set of texture features (1014, 1114). The fourth set of texture features preferably include dimensions selected from a size within a range of about 1 micron to about 10 microns. Preferably, fourth set of texture features 1024 and 1124 are compression molded simultaneously with said first, second, and third sets of texture features into substrate 1010, 1110.

Preferably, flutes and/or ribs (1016, 1018, 1116, 1118) with features and spacing larger than 1 micron are added to the exterior of the cylindrical pillars or cavities defining second set of texture features (1014, 1114) to both add surface area and to increase structural resistance to bending and breaking. The spacing between individual microstructures of fourth set of texture features 1024, 1124 and between individual microstructures of second set of texture features (1014, 1114) is smaller for less viscous liquids and larger for more viscous liquids.

Third set of texture features (1020, 1120) cover both the tops of pillars and bottoms of cavities and the area between the pillars or cavities defining second set of texture features 1314 in a substantially uniform manner. Together the second and third sets of texture features (1014, 1114), (1020, 1120) substantially increase the surface area exposed to the liquid covering the opposite surface from the substrate. Depending on the desired application, the first, second, third and fourth sets of texture features cooperate to increase the surface area of substrate (1010, 1110) to effect at least one of adhesion, friction, hydrophilicity and hydrophobicity of the substrate. In one embodiment, substrate (1010, 1110) has a surface adhesion with a sliding friction force of greater than 50 gr/cm2 when applied against a surface comprised of a hydrophobic/hydrophilic mixture. In a preferred embodiment, the substrate (1010, 1110) has a surface adhesion with a sliding friction force of about 325 gr/cm2 when applied against a surface comprised of a hydrophobic/hydrophilic mixture.

In early studies, the inventors characterized rose petal structures and observed a 'rolling hill' effect in microstructures. Additionally, smaller microstructures were noted as 'hairs' that seemed to contribute strongly to the superhydrophobic effect. In order to best simulate this scheme, the inventors created sinusoidal designs as set forth herein that could reproduce and improve upon rounded microstructure effects seen naturally, starting with a sinusoidal waveform substrate with features from 300 microns diameter and pitch of 100 microns.

The dimensions for the third set of texture features (1020, 1120) include in one embodiment pillars having 3 micrometers diameter, 6 micrometers pitch, and 5 micrometers tall. The second set of texture features (1014, 1114) in one embodiment includes fluted microstructure pillars that are at least 35 micrometers in diameter, 35 micrometers tall, and 10 micrometers spacing. When overlapped together, the second and third sets of micro features (1014, 1114, 1020, 1120) are formed along an axis normal to the surface of the sinusoidal waveform features. These are also maintained multidimensionally over the round.

To improve the superhydrophobic effect found in nature with the rose petal, second set of texture features (1014, 1114) was added with 'fluted' or 'ribbed' features running down the side surface. These fluted and ribbed features that define fourth set of texture features (1024, 1124) simulate the smaller, hair like microstructures of the rose petal to further promote hydrophobicity. Accordingly, each microstructure of said first, second, third and fourth sets of texture features have a respective pitch, height/depth, and diameter, and wherein are arranged so that liquids penetrate between at least said first and second sets of texture features in a Wenzel fully wetted state when applied against a liquid covered surface to promote adhesion between the substrate and the adjacent surface. Preferably, the sinusoidal waveform of the first set of texture features includes rounded peaks that facilitate pressure distribution across the substrate when pressed against a liquid covered surface.

Preferably, the second and third sets (1014, 1020, 1114, 1120) of texture features are uniformly distributed across the rounded peaks of first set of texture features to provide increased surface area to first set of texture features. The rounded peaks define areas of increased pressure when the substrate is applied against a liquid covered surface that promote a transition of liquid droplets from a suspended Cassie-Baxter state to a Wenzel fully wetted state among at least said first and second sets of texture features. In a preferred embodiment, first, second and third sets (1012, 1112, 1112, 1114, of texture features allow for liquid penetration to a Wenzel fully wetted state, while the fourth set of texture features (1024, 1124) are constructed and arranged to maintain superhydrophobic characteristics.

The function of the second and third sets of texture features is to create a large surface area simultaneously with spacing wide enough the viscous liquids can flow through the structure at low pressure. Low pressure in this application is defined in the context of the weight associated with liquid droplets being sufficiently to create a Wenzel fully wetted state to promote adhesion of substrate 10 to an adjacent liquid covered surface. Accordingly, the microstructured surfaces of the present invention are designed to facilitate transitions from a Cassie-Baxter suspended droplet state to the Wenzel fully wetted state with a water droplet of greater than 10 texture liters in size.

One function of the sinusoidal waveform of first set of texture features is to further increase the surface area while creating areas of increased pressure at the peaks of the features. These areas of increased surface area wet first, causing a rapid transition from the Cassie-Baxter suspended droplet state to the Wenzel fully wetted state. A second function of the sinusoidal waveform of first set of texture features is to keep the peak pressure low enough and to spread the pressure such that there is little or no penetration through the liquid layer on the surface into the underlying material. The second and third sets of texture features are spread uniformly over the sinusoidal waveform of first set of texture features and are normal to the curve of the surface. That is they are perpendicular to a surface tangent at each point of the microstructure on surface. This ensures that the maximum surface area is created in a structure that can be molded.

Specific Embodiments

Rotus Type I

Figure 12:
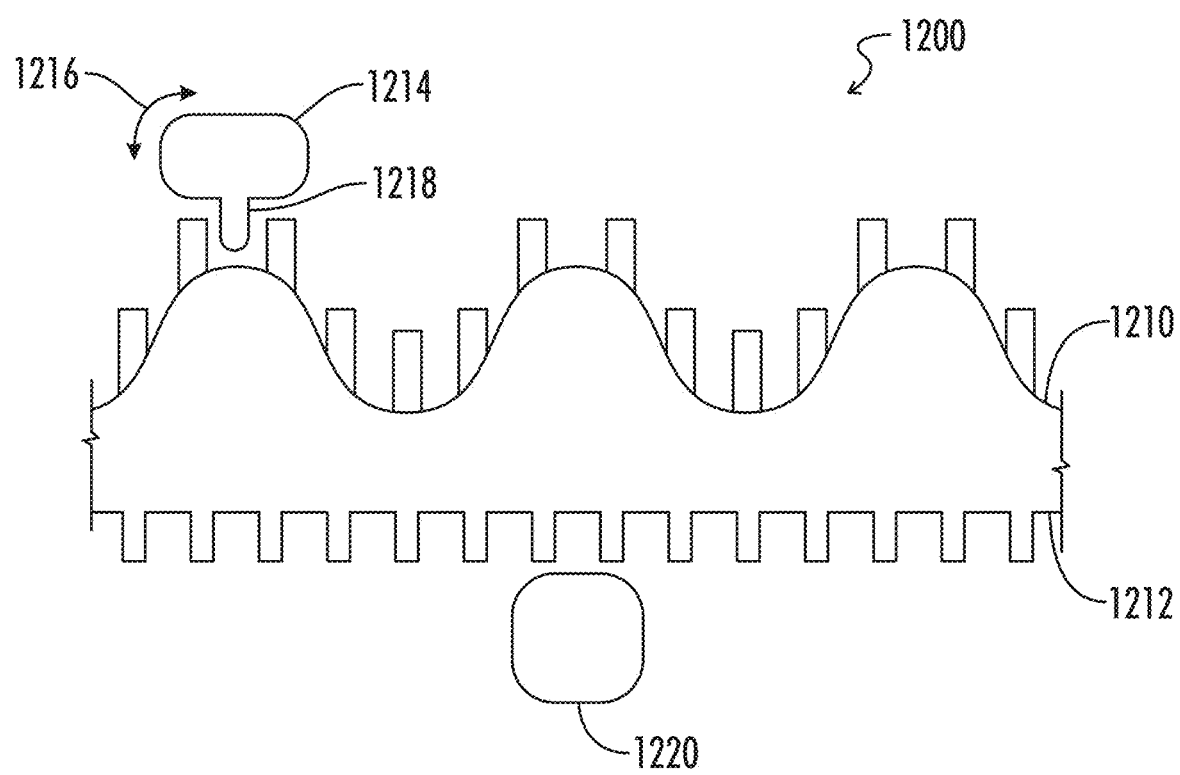
FIG. 12 is a perspective view of a hybrid rotus Type I retraction device according to another embodiment of the invention.

FIG. 12 is a perspective view of a hybrid rotus Type I retraction device according to a third embodiment of the invention. Device 1200 is comprised of rose texture side 1210 and lotus texture side 1212. A rose texture 1210 is characterized by the geometry of a water drop 1214 wherein drop 1214 takes on a spherical shape 1216 characteristic of a superhydrophobic surface. Drop 1214 is immobilized on the surface 1210 due to wicking geometry 1218. A lotus texture 1212 is characterized by the geometry of water drop 1220 wherein the shape is spherical with the absence of a wicking structure analogous to feature 1518. Drop 1220 resists adhesion to surface 1212, and readily rolls off the surface.

Corrugated Type II

Figure 13:
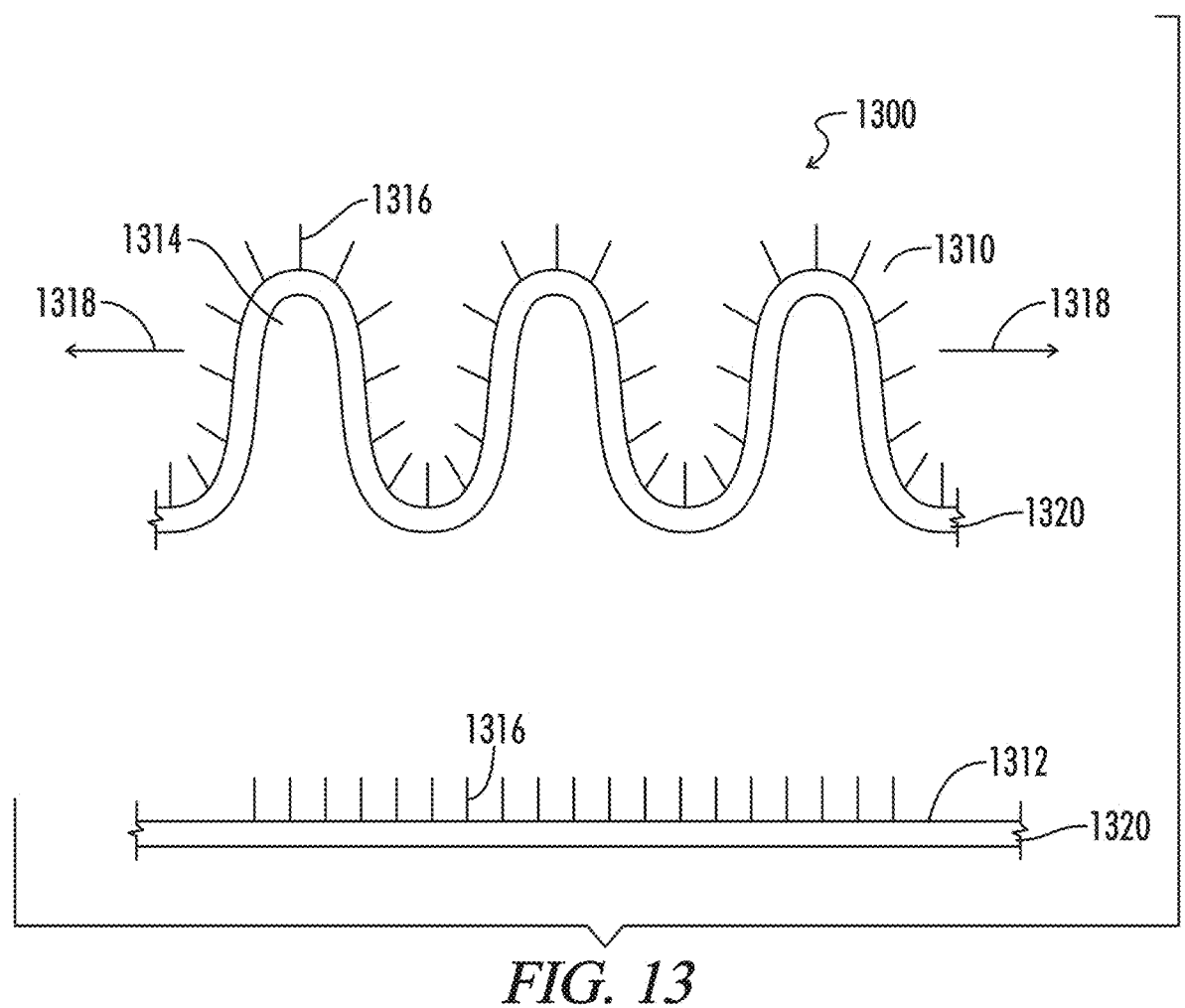
FIG. 13 is a perspective view of a corrugated Type II retraction device according to another embodiment of the invention.

FIG. 13 is a side view of a corrugated Type II retraction device according to a fourth embodiment of the invention. It should be understood a manually actuated Type I version is also possible. Device 1300 can be in two configurations 1310 and 1312. Configuration 1310 is a rose texture configuration and configuration 1312 is a lotus texture configuration. Thus, when in configuration 1610 device 1300 is adhesive, and in configuration 1312 it slides easily. Device 1300 in the corrugated state 1310 has first structure 1314 and second structure 1316. An inflation member 1320 causes device 1600 to move in direction 1318 to transform into configuration 1312 when pressurized.

Area Changing Type II

Figure 14:
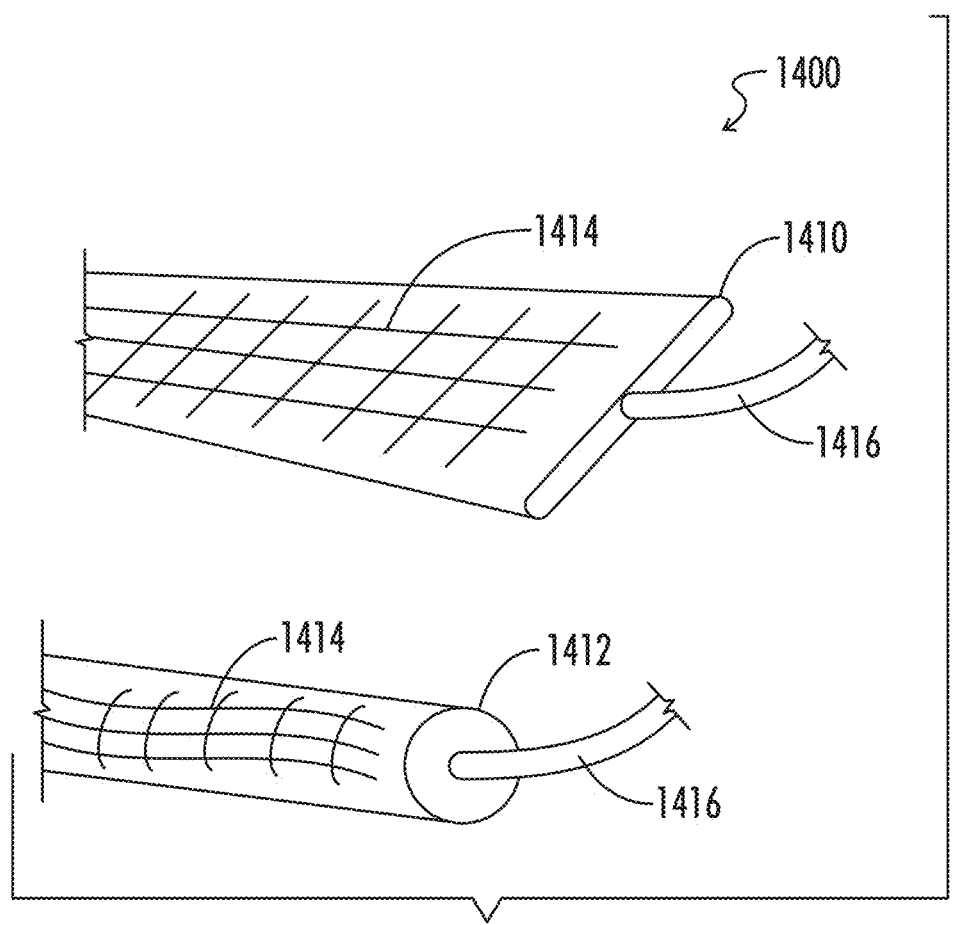
FIG. 14 is a perspective view of a area changing Type II retraction device according to another embodiment of the invention. Device 1400 has surface texture 1414 and can be in two configurations 1410 and 1412. Configuration 1410 is a flat configuration with maximum surface area in contact with a planar surface and configuration 1612 is an inflated configuration with minimum surface area. Thus, when in configuration 1710 device 1700 is adhesive, and in configuration 1412 it slides more easily. An inflation member 1416 causes device 1400 to transform into configuration 1412 when pressurized.

FIG. 14 is a perspective view of a area changing Type II retraction device according to a fifth embodiment of the invention. Device 1400 has surface texture 1314 and can be in two configurations 1310 and 1312. Configuration 1310 is a flat configuration with maximum surface area in contact with a planar surface and configuration 1612 is an inflated configuration with minimum surface area. Thus, when in configuration 1310 device 1300 is adhesive, and in configuration 1312 it slides more easily. An inflation member 1316 causes device 1300 to transform into configuration 1312 when pressurized.

Area Changing Type I

Figure 15:
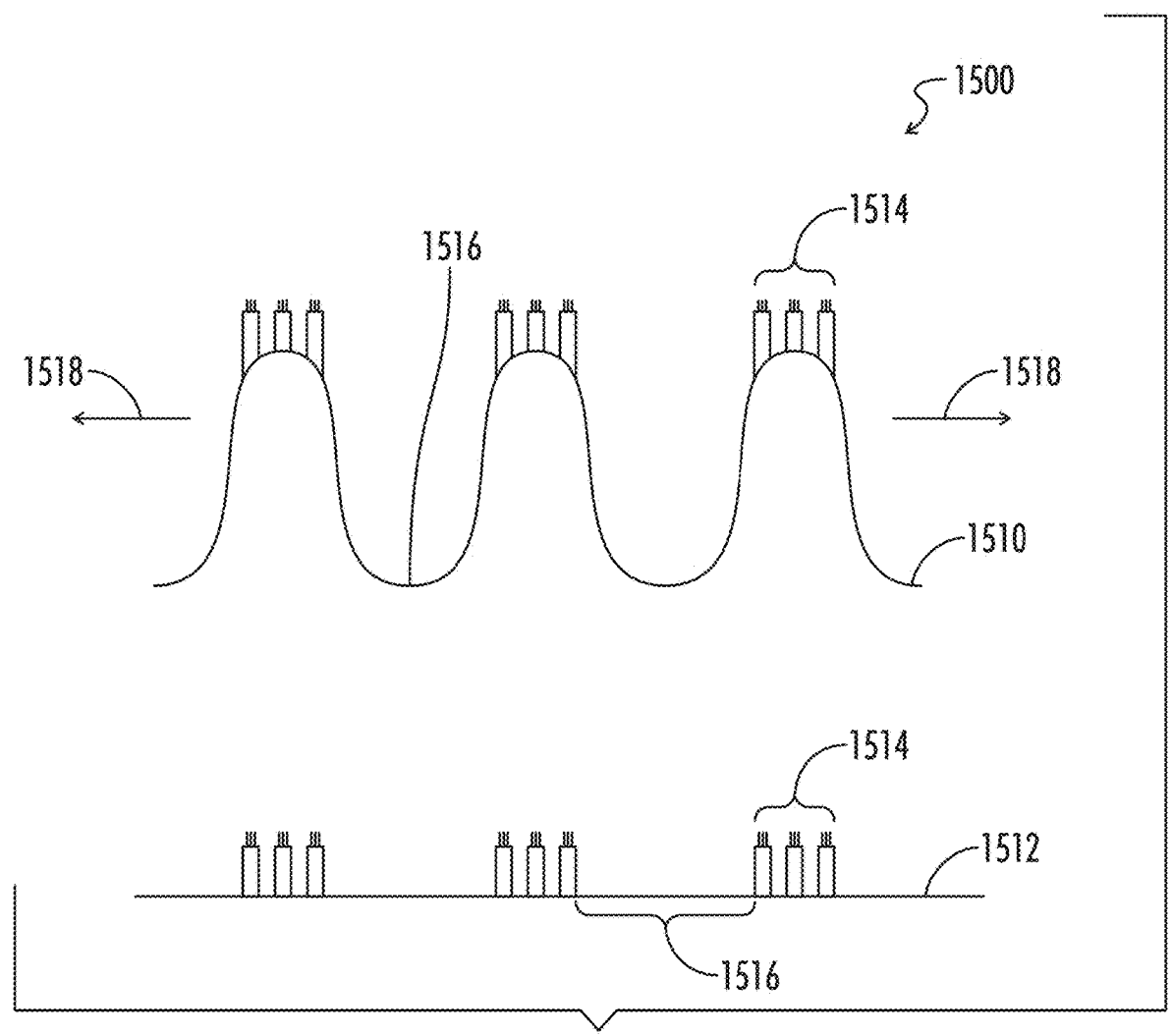
FIG. 15 is a side view of a hybrid area changing Type I retraction device 1500 where the textured area 1514 is unchanging according to a sixth embodiment of the invention. Device 1500 assumes two bistable configurations 1510 and 1512. In configuration 1510 rose petal texture 1514 is the only surface presented to another surface to which device 1500 is to adhere. The contact surface area in configuration 1510 is the sum of the areas of 1514. The area 1516 is smooth, and the area of configuration 1512 is larger than the area of configuration 1510. The area of configuration 1512 is the sum of the areas 1514 and 1516. Configuration 1512 is achieved by pulling configuration 1510 in the directions 1518.

FIG. 15 is a side view of a hybrid area changing Type I retraction device 1500 where the textured area 1514 is unchanging according to a sixth embodiment of the invention. Device 1500 assumes two bistable configurations 1510 and 1512. In configuration 1510 rose petal texture 1514 is the only surface presented to another surface to which device 1500 is to adhere. The contact surface area in configuration 1510 is the sum of the areas of 1514. The area 1516 is smooth, and the area of configuration 1512 is larger than the area of configuration 1510. The area of configuration 1512 is the sum of the areas 1514 and 1516. Configuration 1512 is achieved by pulling configuration 1510 in the directions 1518.

Pincer Type II

Figure 16:
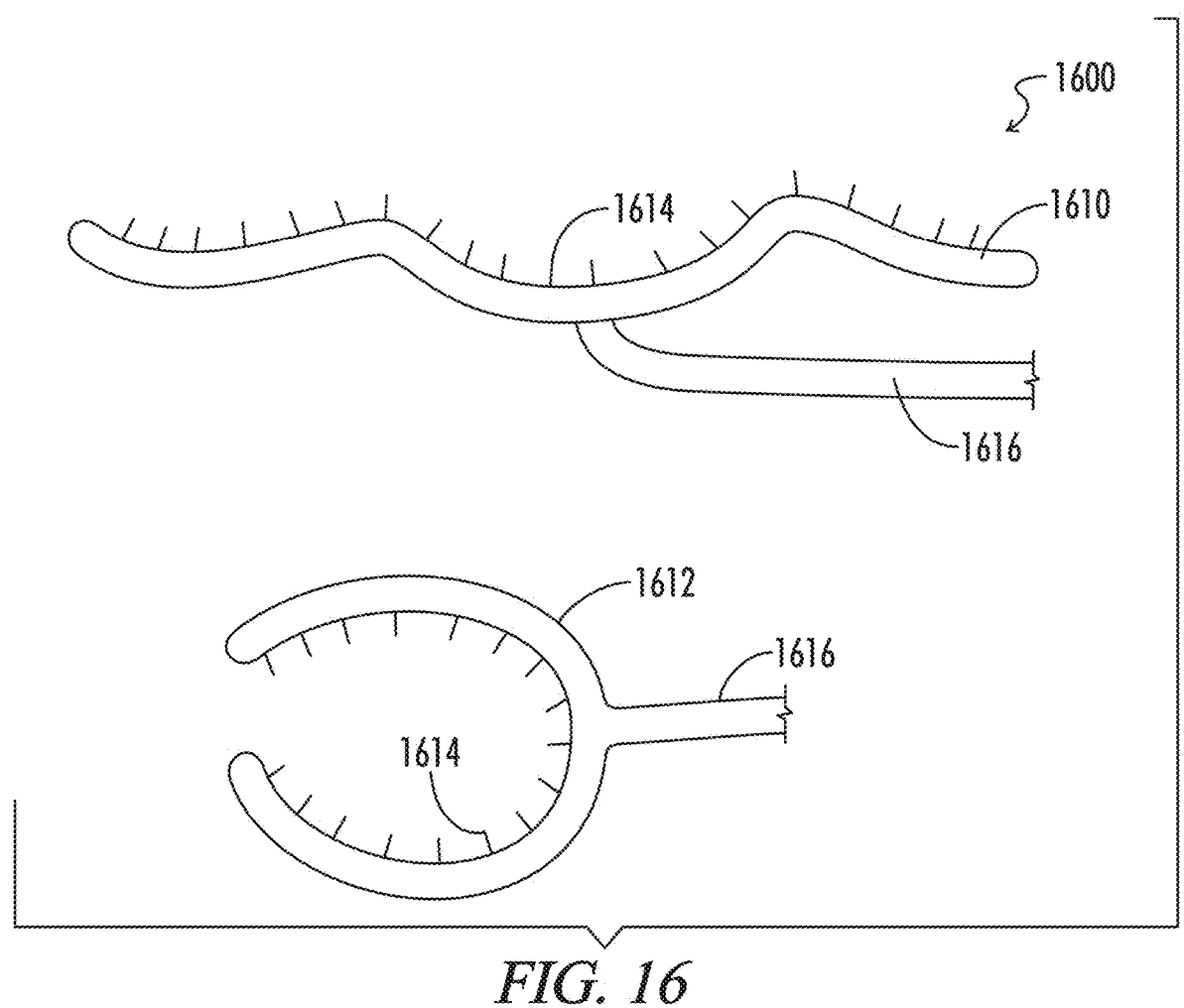
FIG. 16 is a perspective view of a pincer movement Type II retraction device 1600 according to a seventh embodiment of the invention. Device 1600 has a relaxed, conformable state 1610 and rigid pinching state 1612. Transformation from state 1610 to state 1612 is achieved by inflation means 1616. Features 1614 are comprise a rose petal adhesive surface.

FIG. 16 is a perspective view of a pincer movement Type II retraction device 1600 according to a seventh embodiment of the invention. Device 1600 has a relaxed, conformable state 1610 and rigid pinching state 1612. Transformation from state 1610 to state 1612 is achieved by inflation element 1616. Features 1614 comprise a rose petal adhesive surface.

Figure 17:
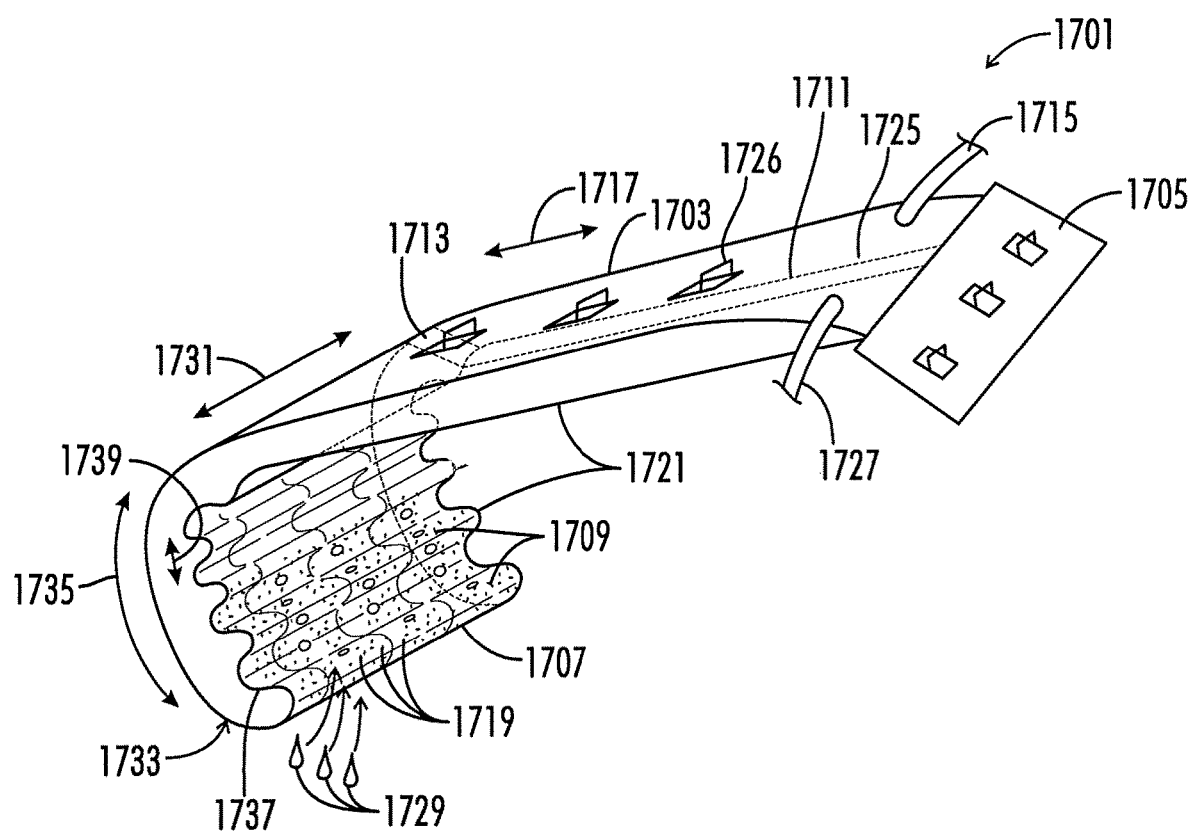
FIG. 17 depicts a retractor comprising an arm having the microtextured surface of the present disclosure disposed on a portion thereof.

FIG. 17 depicts a retractor 1701 comprised of arm 1703 and surgical anchor 1705. The surgical anchor 1705 enables the surgeon to anchor the retractor 1701 to perioperative surgical dressing. The proximal end 1707 of the retractor 1701 possesses superhydrophobic surface 1709. Detailed examples of superhydrophobic surface are depicted and described above. Optionally, the retractor may comprise an inflation element 1711 comprised on a hollow section 1713 that can be pressurized via tube 1715. As depicted, when hollow section 1713 is inflated the retractor becomes rigid and straight along direction 1717. Optionally, the retractor may comprise a suction bladder comprised of a series of holes 1719 providing throughput from tissue contacting side 1721 to internal suction volume 1723. The suction bladder is comprised of the tissue contacting side 1721 and an external side 1725. External side 1725 may possess tabs 1726 to which a surgeon may suture a stay line or grasp to position retractor 1 relative to a tissue surface. A suction tube 1727 attached to the suction bladder provides suction and draws tissue fluid 1729 into the suction bladder. Optionally retractor 1 may possess a preformed shape such that the width 1731 is straight and the length 1733 is curved with radius of curvature 1735. Optionally, the retractor 1701 possesses a tissue contacting surface 1721 which is corrugated 1737. The corrugation frequency 1739 can be adjusted through inflation element 1711, such that increased inflation decreases frequency 1739 and increases length 1733.

All references cited herein are hereby incorporated by reference in their entirety.

We claim:

1. A microstructured retractor comprising at least one arm having a surface which is reversibly deformable via an inflation element engaged with the at least one arm such that when inflated a corrugation frequency of the surface reversibly changes from a first state to a second state, the surface in the first state including a microstructured Cassie-Baxter surface and the surface in the second state including a microstructured Wenzel-Cassie surface, and wherein the at least one arm is configured to be placed on a wet surface such that when in the second state, the shear force required to move the microstructured retractor along the wet surface exceeds the applied normal force, wherein the microstructured surfaces each comprise at least two microstructure features of different spatial scales disposed in a hierarchical pattern.

2. The microstructured retractor of claim 1, wherein the inflation element provides adjustable rigidity to the microstructured retractor.

3. The microstructured retractor of claim 1, wherein a suction element is attached to the microstructured retractor to provide fluid removal while the microstructured retractor is in use.

4. The microstructured retractor of claim 1, wherein the at least one arm comprises a shorter dimension defining a width and a longer dimension defining a length, and wherein the at least one arm further comprises a flexible material capable of being preformed with an innate curvature, wherein the width has essentially zero curvature and wherein a radius of curvature in the length dimension is less than the length.

5. The microstructured retractor of claim 1, wherein the at least one arm is corrugated in a direction such that when the at least one arm is placed on the wet surface, only a portion of the surface is in contact with the wet surface, and wherein the corrugation is adjustable by deformation of the at least one arm so as to change the amount of the surface in contact with the wet surface.

6. The microstructured retractor of claim 5, wherein the inflation element comprises a valve such that an inflation volume of the inflation element can be controlled.

7. The microstructured retractor of claim 6, wherein an additional inflation element is engaged therewith that reversibly stiffens the microstructured retractor when inflated.

8. The microstructured retractor of claim 5, wherein at least a portion of the surface has contact angle hysteresis greater than 5 degrees when in contact with the wet surface.

9. The microstructured retractor of claim 1, wherein the surface is a rose petal-like surface.

10. The microstructured retractor of claim 1, wherein the surface is a lotus petal-like surface.

11. The microstructured retractor of claim 1, wherein at least a portion of the surface has a contact angle hysteresis greater than 5 degrees when in contact with the wet surface.

12. The microstructured retractor of claim 1, wherein the surface comprises at least three microstructured features of at least three different spatial scales disposed in a hierarchical pattern.

* * * * *